(12) United States Patent
Yao et al.

(10) Patent No.: US 11,982,637 B2
(45) Date of Patent: May 14, 2024

(54) SENSORS COMPRISING ELECTRICALLY-CONDUCTIVE PROTEIN NANOWIRES

(71) Applicant: University of Massachusetts, Boston, MA (US)

(72) Inventors: Jun Yao, Boston, MA (US); Derek R. Lovley, Amherst, MA (US); Alexander Smith, Boston, MA (US); Xiaomeng Liu, Boston, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 17/302,063

(22) Filed: Apr. 22, 2021

(65) Prior Publication Data

US 2021/0341406 A1 Nov. 4, 2021

Related U.S. Application Data

(60) Provisional application No. 63/014,043, filed on Apr. 22, 2020.

(51) Int. Cl.
| | |
|---|---|
| *G01N 27/12* | (2006.01) |
| *A61B 5/08* | (2006.01) |
| *G01N 33/00* | (2006.01) |

(52) U.S. Cl.
CPC ........... *G01N 27/127* (2013.01); *A61B 5/082* (2013.01); *G01N 27/121* (2013.01); *G01N 33/0054* (2013.01); *A61B 2562/0285* (2013.01)

(58) Field of Classification Search
CPC .............. G01N 27/127; G01N 27/121; G01N 33/0054; A61B 5/082; A61B 2562/0285;
(Continued)

(56) References Cited

U.S. PATENT DOCUMENTS

| | | |
|---|---|---|
| 7,498,155 B2 | 3/2009 | Lovley et al. |
| 8,232,584 B2 | 7/2012 | Lieber |

(Continued)

FOREIGN PATENT DOCUMENTS

| | | | |
|---|---|---|---|
| CN | 1527051 A | * 9/2004 | ............. G01N 27/62 |
| CN | 108365776 A | 8/2018 | |

(Continued)

OTHER PUBLICATIONS

Ueki T., et al., "Decorating the Outer Surface of Microbially Produced Protein Nanowires with Peptides," ACS Synth Biol. X;8(8): 1809-1817 (2019).

(Continued)

*Primary Examiner* — Farhana A Hoque
*Assistant Examiner* — Dilara Sultana
(74) *Attorney, Agent, or Firm* — Hamilton, Brook, Smith & Reynolds, P.C.

(57) ABSTRACT

A gas sensor includes a biomaterial comprising electrically-conductive protein nanowires and at least two electrodes. The at least two electrodes are in operative arrangement with the protein nanowires and configured to provide a signal indicative of a change in conductivity of the protein nanowires. The conductivity of the protein nanowires is responsive to a change in concentration of a gas exposed to the biomaterial, such as ammonia, or to a change in relative humidity.

19 Claims, 19 Drawing Sheets
(3 of 19 Drawing Sheet(s) Filed in Color)

Specification includes a Sequence Listing.

(58) Field of Classification Search
CPC .............. A61B 5/0816; A61B 5/4875; A61B 2562/029; A61B 2562/164
See application file for complete search history.

(56) References Cited

U.S. PATENT DOCUMENTS

| | | | |
|---|---|---|---|
| 8,608,921 | B2 | 12/2013 | Li |
| 8,729,233 | B2 | 5/2014 | Reguera et al. |
| 8,846,890 | B2 | 9/2014 | Reguera et al. |
| 9,102,521 | B2 | 8/2015 | Lieber et al. |
| 9,234,508 | B2 | 1/2016 | Sahin |
| 9,601,227 | B2 | 3/2017 | Reguera et al. |
| 9,697,460 | B2 | 7/2017 | Collins et al. |
| 9,784,249 | B2 | 10/2017 | Li |
| 10,083,974 | B1 | 9/2018 | Huang et al. |
| 10,311,357 | B2 | 6/2019 | Nugent et al. |
| 10,388,370 | B2 | 8/2019 | Schmidt et al. |
| 10,684,244 | B2 | 6/2020 | Chen |
| 10,741,778 | B2 | 8/2020 | Kirsch et al. |
| 11,043,265 | B2 | 6/2021 | Li et al. |
| 11,063,227 | B2 | 7/2021 | Kirsch et al. |
| 11,066,449 | B2 | 7/2021 | Lovley et al. |
| 11,133,058 | B1 | 9/2021 | Philip et al. |
| 11,631,824 | B2 | 4/2023 | Yao et al. |
| 2006/0113880 | A1 | 6/2006 | Pei |
| 2007/0157967 | A1 | 7/2007 | Mershin et al. |
| 2008/0283799 | A1 | 11/2008 | Alden et al. |
| 2009/0188784 | A1 | 7/2009 | Lee |
| 2010/0119879 | A1 | 5/2010 | Girguis |
| 2012/0053319 | A1 | 3/2012 | Reguera et al. |
| 2014/0239237 | A1* | 8/2014 | Reguera .................. H01B 1/12 252/514 |
| 2014/0330337 | A1 | 11/2014 | Linke et al. |
| 2014/0336357 | A1 | 11/2014 | Reguera et al. |
| 2018/0007819 | A1 | 1/2018 | Vajo |
| 2018/0195997 | A1* | 7/2018 | Li .......................... C01B 32/159 |
| 2018/0202964 | A1 | 7/2018 | Alam et al. |
| 2018/0371029 | A1* | 12/2018 | Lovley ................. C07K 14/195 |
| 2019/0148085 | A1 | 5/2019 | Kim |
| 2020/0090830 | A1 | 3/2020 | Lovley et al. |
| 2021/0002332 | A1 | 1/2021 | Malvankar |
| 2021/0070811 | A1 | 3/2021 | Reguera et al. |
| 2021/0336169 | A1 | 10/2021 | Yao et al. |
| 2021/0344286 | A1 | 11/2021 | Yao et al. |
| 2023/0040959 | A1 | 2/2023 | Lovley et al. |
| 2023/0160885 | A1 | 5/2023 | Lovley et al. |

FOREIGN PATENT DOCUMENTS

| | | | | |
|---|---|---|---|---|
| KR | 101203181 | B1 * | 11/2012 | .............. B82B 3/00 |
| KR | 101768665 | B1 * | 12/2016 | ............ G01N 27/12 |
| WO | 2013033456 | A2 | 3/2013 | |
| WO | 2017/015306 | A2 | 1/2017 | |
| WO | WO-2019144931 | A1 * | 8/2019 | ............ B82Y 40/00 |
| WO | WO-2019169331 | A1 * | 9/2019 | ........... C07K 14/195 |
| WO | 2020069523 | A1 | 4/2020 | |
| WO | 2020/191281 | A1 | 9/2020 | |
| WO | 2021102327 | A1 | 5/2021 | |

OTHER PUBLICATIONS

Ueki T., et al., "An *Escherichia coli* Chassis for Production of Electrically Conductive Protein Nanowires," 9(3):647-654 ACS Synth Biol. (2020).
Liu X., et al., "Power Generation from Ambient Humidity Using Protein Nanowires," Nature; 578: 550-554 (2020).
Lovley, D. R., Electrically conductive pili: Biological function and potential applications in electronics, Curr. Opin. Electrochem. 4, 190 (2017).
Lovely,D., et al., "Geobacter Protein Nanowires", Front. Microbiol. 10, 2078 (2019).
Adhikari, R. Y., et al., Conductivity of individual Geobacter pili, RSC Adv. 6, 8354 (2016).
Tan, Y. et al. Expressing the Geobacter metallireducens PilA in Geobacter sulfurreducens Yields Pili with Exceptional Conductivity. MBio. 8, 02203-16 (2017).
Adhikari, R. Y., et al. Conductivity of individual Geobacter pili. RSC Advances 6, 8354-8357 (2016).
Malvankar, N.S., et al., "Tunable Metallic-Like Conductivity in Microbial Nanowire Networks", Nat. Nanotechnol. 6, 573-579 (2011).
Milano, Gianluca, et al, "Self-limited single nanowire systems combining all-in-one memristive and neuromorphic functionalities", Dec. 2018, Nature Communications, Article No. 5151. pp. 1-10 (Year: 2018).
Fu, Tianda, et al, "Bioinspired bio-voltage memristors", Nature Communications, 2020, Article pp. 1-10 (Year: 2020).
Kumar, Anish, et al, "Protein Biosensors Based on Polymer Nanowires, Carbon Nanotubes and Zinc Oxide Nanorods", Sensors Journal, May 2011, 5087-5111 (Year: 2011).
Zhou, Jiangfeng, et al, "Development of nanowire-modified electrodes applied in the locally enhanced electric field treatment (LEEFT) for water disinfection", 2020, Journals of Materials Chemistry. Article, 12262-12277 (Year: 2020).
Liu, Xiaomeng, et al, "Power generation from ambient humidity using protein nanowires", Feb. 2020, pp. 550-556 (Year: 2020).
Cui, Yi, et al, "Nanowire Nanosensors for Highly Sensitive and Selective Detection of Biological and Chemical Species", Aug. 2021, Science Magazine, vol. 293, pp. 1289-1292. (Year: 2021).
Notification of Transmittal of the International Search Report and Written Opinion of International Application No. PCT/US2019/053882, titled: "Electric Power Generation From Ambient Humidity Using Protein Nanowires," dated Jan. 17, 2020.
Notification Concerning Transmittal of International Preliminary Report on Patentability for International Application No. PCT/US2019/053882, entitled: "Electric Power Generation from Ambient Humidity Using Protein Nanowires," dated Apr. 8, 2021.
Wu, S., et al, "Regulation of expression of pilA gene in Myxococcus xanthus," Journal of Bacteriology, 179(24):7748-7758 (1997).
Yang, Yen-Chun, et al, "PilR enhances the sensitivity of *Xanthomonas axonopodis* pv. citri to the infection of filamentous bacteriophage Cf," Current Microbiology, 48(4):251-261 (2004).
Balberg et al, "Excluded vol. and its relation to the onset of percolation," Physical Review B, vol. 30, No. 7, Oct. 1, 1984.
Guo et al, "Flexible transparent conductors based on metal nanowire networks," Elsevier, Materials Today, vol. m, No. 3, Apr. 2015.
Malvankar et al., "Structural Basis for Metallic-Like Conductivity in Microbial Nanowires", mBio, vol. 4, Issue 2, Mar./Apr. 2015, pp. mBio 6:e00084-00015 (cited in specification on p. 15).
Vargas et al., "Aromatic Amino Acids Required for Pili Conductivity and Long-Range Extracellular Electron Transport in Geobacter sulfurreducens", mBio, vol. 4, Issue 2, Mar./Apr. 2013, pp. 1-6 (cited in specification on p. 14).
Gerald F. Audette et al, "Protein Nanotubes: From Bio-nanotech towards Medical Applications", Jun. 2019, Biomedicines Journal, vol. 7/46. (Year: 2019).
Guterman, et al., "Toward Peptide-Based Bioelectronics: Reductionist Design of Conductive Pili Mimetics," Bioelectron Med (Lond.) May 2018: 1(2): 131-137.
Jerry A. Fereira et al, "Tunneling explains efficient electron transport via protein junctions", Weizmann Institute of SCience Reports, Nov. 2017, vol. 114, No. 20 (Year: 2017).
Liu, et al., "Biological Synthesis of High-Conductive Pili in Aerobic Bacterium Pseudomonas Aeruginosa," Applied Microbiology and Biotechnology (2019) 103:1535-1544.
Rico, A.L. et al., "Functional reconstitution of the type IVa pilus assembly system from enterohaemorrhagic *Escherichic coli*," Mol. Microbiol., vol. 111; No. 3; 732-749 (2019).
Ueki, Toshiyuki, et al. "Decorating microbially produced protein nanowires with peptide ligands." bioRxiv (2019): 590224.
Amrin et al., "Electrical properties and conduction mechanism in carboxylfunctionalized multiwalled carbon rianotubes/poly(vinyl alcohol) composites," J Mater Sci (2016) 51:2453-2464_.
Balberg et al., "Excluded volume and its relation to the onset of percolation," Physical Review B, vol. 30, No. 7, Oct. 1, 1984.

(56) References Cited

OTHER PUBLICATIONS

Bauhofer et al., "A review and analysis of electrical percolation in carbon nanotube polymer composites," Elsevier, Composites Science and Technology 69 (2009) 1486-1498.
Byrne et al., "Recent Advances in Research on Carbon Nanotube-Polymer Composites," Advanced Materials, 2010,22, 1672-1688.
Celzard et al.,"Critical concentration in percolating systems containing a high-aspect-ratio filler," Physical Review B, vol. 53, No. 10, Mar. 1, 1996.
Chandrakishore et al., "Facile synthesis of carbon nanotubes and their use in the fabrication of resistive switching memory devices," RSC Advances, 2014, 4, 9905-9911.
Chen et al., "Electrical Conductivity of Polymer Blends of Poly(3,4-ethylenedioxythiophene) : Poly styrenesulfonate) :N-Methyl-2-pyrrolidinone and Polyvinyl Alcohol," Journal of Applied Polymer Science, vol. 125, ?134-3141 (2012).
Childers et al., "Geobacter metallireducens accesses insoluble Fe(III) oxide by chemotaxis" Nature, vol. 416, Apr. 18, 2002, pp. 767-769 (cited in specification on p. 15).
Cho et al., "Synthesis and electrical properties of polymer composites with polyaniline nanoparticles," Elsevier, Materials Science and Engineering C 24 (2004) 15-18.
Coppi et al., "Development of a Genetic System for Geobacter sulfurreducens", Applied and Environmental Microbiology, vol. 67, No. 7, Jul. 2001, pp. 3180-3187 (cited in specification on p. 15).
Gangopadhyay et al., "Polyaniline-poly(vinyl alcohol) conducting composite: material with easy processability and novel application potential," Elsevier, Synthetic Metals 123 (2001) 21-31.
Green et al., "Conductive Hydrogels: Mechanically Robust Hybrids for Use as Biomaterials," Macromolecular Bioscience, 2012, 12, 494-501.
Guo et al., "Flexible transparent conductors based on metal nanowire networks," Elsevier, Materials Today, vol. rn, No. 3, Apr. 2015.
Li et al., "Ordered multiphase polymer nanocomposites for high-performance solid-state supercapacitors," Elsevier, Composites: Part B 71 (2015), 40-44.
Liu et al., "Flexible supercapacitor sheets based on hybrid nanocomposite materials," Elsevier, Nano Energy (2013) pp. 133-137.
Liu et al., "A Geobacter sulfurreducens Strain Expressing Pseudomonas aeruginosa Type IV Pili Localizes OmcS on Pili but Is Deficient in Fe(III) Oxide Reduction and Current Production", Applied and Environmental Microbiology, vol. go, No. 3, Feb. 2014, pp. 1219-1224 (cited in specification on p. 14).
Lovley et al., "Seeing is believing: novel imaging techniques help clarify microbial nanowire structure and function", Environmental microbiology, vol. 17, Issue 7, 2015, pp. 2209-2215 (cited in specification on p. 15).
Lovley, "e-Biologics: Fabrication of Sustainable Electronics with 'Green' Biological Materials," American Society for Microbiology, May/Jun. 2017, vol. 8, Issue 3 e00695-17.
Makhlouki et al., "Transport Properties in Polypyrrole-PVA Composites: Evidence for Hopping Conduction," Journal of Applied Polymer Science, vol. 44, 443-446 (1992).
Malhofer et al., "Direct visualization of percolation paths in carbon nanotube/polymer composites," Elsevier, Organic Electronics 45 (2017) 151-158.
Malvankar et al., "Tunable metallic-like conductivity in microbial nanowire networks," Nature Nanotechnology vol. 6, Sep. 2011.
Malvankar et al., "Lack of cytochrome involvement in long-range electron transport through conductive biofilms and nanowires of Geobacter sulfurreducens", Energy & Environmental Science, vol. 5, 2012, pp. 8651-8659 (cited in specification on p. 14).
Malvankar et al., "Microbial nanowires for bioenergy applications", Current Opinion in Biotechnology, vol. 27, 2017, pp. 88-95 (cited in specification on p. 15).
Malvankar et al., "Microbial Nanowires: A New Paradigm for Biological Electron Transfer and Bioelectronics", ChemSusChem Concepts, vol. 5, 2012, pp. 1039-1046 (cited in specification on p. 14).

Malvankar et al., "Structural Basis for Metallic-Like Conductivity in Microbial Nanowires", mBio, vol. 4, Issue 2, Mar./Apr. 2015, pages . mBio 6:e00084-00015 (cited in specification on p. 15).
Malvankar et al., "Structural Basis for Metallic-Like Conductivity in Microbial Nanowires," Mar./Apr. 2015 mBio vol. 6 Issue 2 e00084-15.
Malvankar et al., "Tunable metallic-like conductivity in microbial nanowires", Nature Nanotechnology, vol. 6, Sep. 2011, pp. 573-579 (cited in specification on p. 14).
Malvankar et al., Visualization of charge propagation along individual pili proteins using ambient electrostatic force microscopy Nature Nanotechnology, vol. 9, Dec. 2014, pp. 1-10 (cited in specification on p. 15).
Miaudet et al., "Thermo-electrical properties of PVA-nanotube composite fibers," ELSEVIER, ScienceDirect, Polymer 48 (2007) 4068-4074.
Nevin et al., "Anode Biofilm Transcriptomics Reveals Outer Surface Components Essential for High Density Current 14 Production in Geobacter sulfurreducens Fuel Cells", PloS ONE, vol. 4, Issue 5, May 2009, pp. 1-11 (cited in specification on p. 15).
Nevin et al., "Power output and columbic efficiencies from biofilms of Geobacter sulfurreducens comparable to mixed 15 community microbial fuel cells", Environmental Microbiology, vol. 10, No. 10, 2008, pp. 2505-2514 (cited in specification on p. 15).
Ogura et al.,"A Conductive and Humidity-Sensitive Composite Film Derived from Poly(o-phenylenediamine) and Polyvinyl Alcohol," J_ Electrochem_ Soc., vol. 142, No. 9, Sep. 1995.
Reardon et al., "Structure of the Type IVa Major Pilin from the Electrically Conductive Bacterial Nanowires of Geobacter sulfurreducens", Journal of Biological Chemistry, vol. 288, No. 41, 2013, p. 29260-29266.
Reguera et al., "Extracellular electron transfer via microbial nanowires", Nature, vol. 435, Jun. 2005, p. 1098 1101 (cited in specification on p. 15).
Richter, "Mutational Analysis of Geopilin Function in Geobacter Sulfurreducens", 2011,[retrieved on line Dec. J8, 2016] at <http://scholarworks.umass.edu/open_access_dissertations/378/, 157 pages.
Shih et al., "Tryptophan-Accelerated Electron Flow Through Proteins", Science, vol. 320, Jun. 27, 2008, pp. 1760-1762 (cited in specification on p. 15).
Sun et al.,"Flexible polydimethylsiloxane/multi-walled carbon nanotubes membranous metacomposites with negative permittivity," Elsevier, Polymer 125 (2017) 50-57.
Tan et al., "Synthetic Biological Protein Nanowires with High Conductivity," small 2016, 12, No. 33, 4481-4485.
Tang et al., "Effect of pH on Protein Distribution in Electrospun PVA/BSA Composite Nanofibers," 2012 American Chemical Society, 1269-1278.
Tseng et al.,"Digital memory device based on tobacco mosaic virus conjugated with nanoparticles," nature nanotechnology, vol. 1., Oct. 2006, pp. 72-77.
Vargas et al., "Aromatic Amino Acids Required for Pill Conductivity and Long-Range Extracellular Electron Transport in Geobacter sulfurreducens", mBio, vol. 4, Issue 2, Mar./Apr. 2013, pp. 1-6 (cited in specification on p. 14).
Walker et al., "Electrically conductive pili from pilin genes of phylogenetically diverse microorganisms," The ISME Journal (2018) 12, 48-58.
Yang, "Synthesis and characterization of the cross-linked PVA/TiO2 composite polymer membrane for alkaline DMFC," Elsivier, Journal of Membrane Science 288 (2007) 51-60.
Zezelj et al., Publisher's Note: From percolating to dense random stick networks: Conductivity model nvestigation (Phys. Rev_ B 86, 134202 (2012). Physical Review B 86, 139904(E) (2012).
Zhang et al., "Composite films of nanostructured polyaniline with poly(vinyl alcohol)," Elsevier, Synthetic Metals 128 (2002) 83-89.
Zhang et al., "Electrical and dielectric behaviors and their origins in the three-dimensional polyvinyl alcohol/MWCNI pomposites with low percolation threshold," Elsevier, Carbon 47 (2009) 1311-1320.

\* cited by examiner

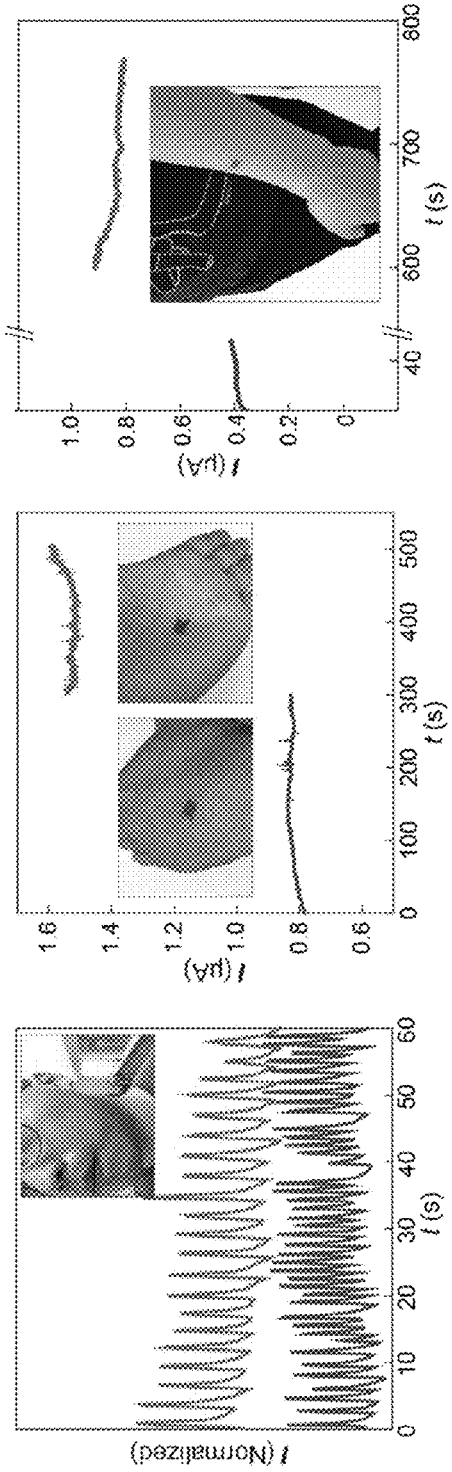
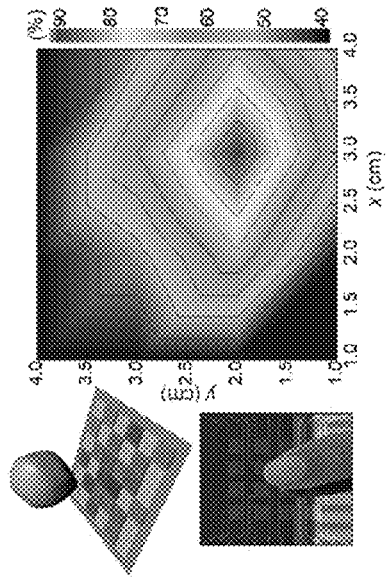
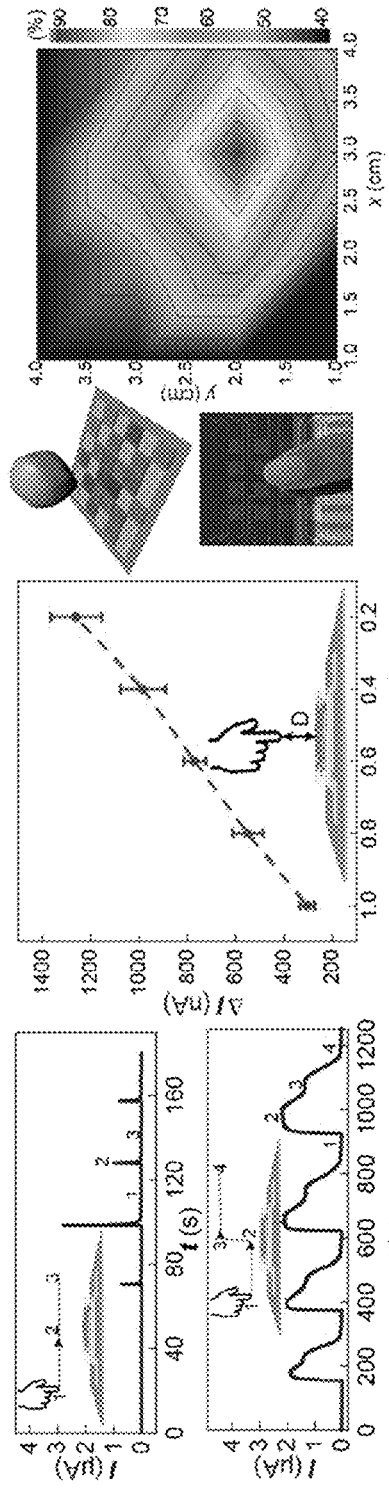
FIG. 14A
FIG. 14B
FIG. 14C
FIG. 14D
FIG. 14E
FIG. 14F

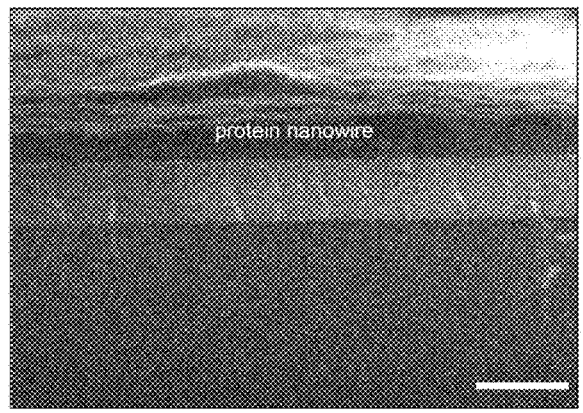
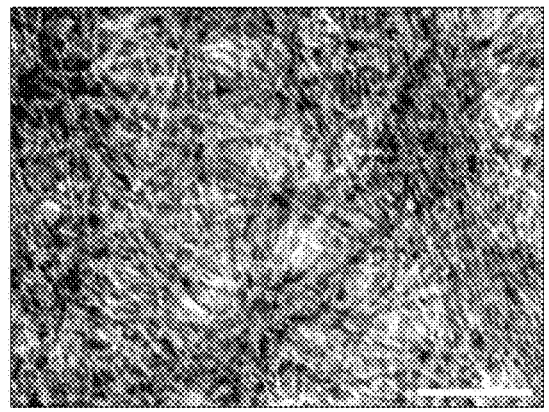
FIG. 19A
FIG. 19B
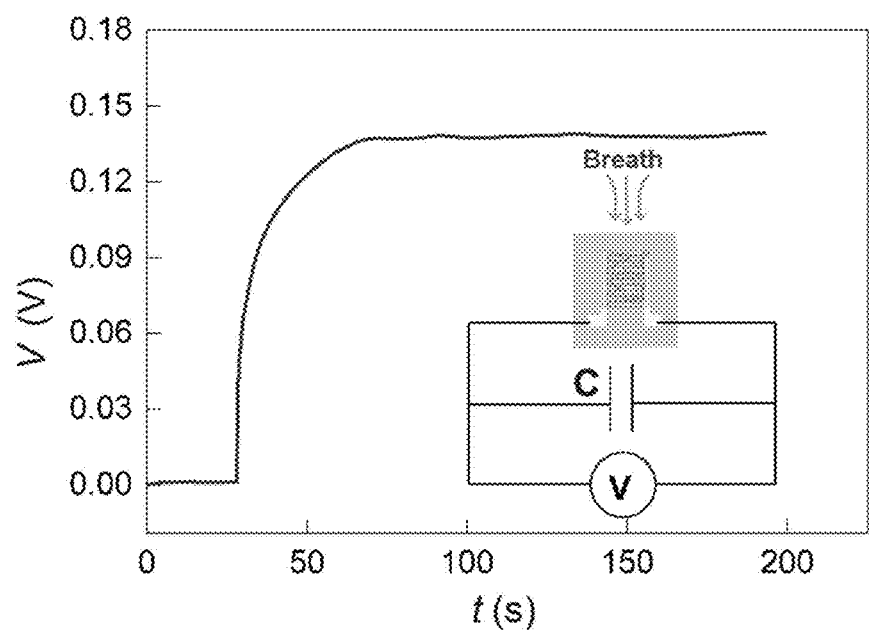
FIG. 20

SEQUENCE LISTING

<160> NUMBER OF SEQ ID NOS: 33

<210> SEQ ID NO 1
<211> LENGTH: 61
<212> TYPE: PRT
<213> ORGANISM: Geobacter sulfurreducens

<400> SEQUENCE: 1

```
Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60
```

<210> SEQ ID NO 2
<211> LENGTH: 59
<212> TYPE: PRT
<213> ORGANISM: Geobacter metallireducens

<400> SEQUENCE: 2

```
Phe Thr Leu Ile Glu Leu Leu Ile Val Val Ala Ile Ile Gly Ile Leu
1               5                   10                  15

Ala Ala Ile Ala Ile Pro Gln Phe Ala Ala Tyr Arg Gln Lys Ala Phe
            20                  25                  30

Asn Ser Ala Ala Glu Ser Asp Leu Lys Asn Thr Lys Thr Asn Leu Glu
        35                  40                  45

Ser Tyr Tyr Ser Glu His Gln Phe Tyr Pro Asn
    50                  55
```

<210> SEQ ID NO 3
<211> LENGTH: 119
<212> TYPE: PRT
<213> ORGANISM: Calditerrivibrio nitroreducens

<400> SEQUENCE: 3

```
Phe Thr Leu Ile Glu Leu Leu Val Val Ala Ile Ile Ala Ile Leu
1               5                   10                  15

Ala Ala Ile Ala Ile Pro Gln Phe Ala Lys Tyr Arg Glu Asn Ala Ala
            20                  25                  30

Lys Ala Ser Ala Val Ala Asp Ala Lys Asn Ile Ala Thr Ala Ile Glu
        35                  40                  45

Ser Tyr Tyr Ala Asp Thr Gln Ser Phe Pro Ser Ser Ile Ser Asp Gly
    50                  55                  60

Ser Ile Val Pro Leu Gly Thr Gln Thr Phe Ser Leu Ser Lys Asn Asn
65                  70                  75                  80

Ser Phe Lys Gly Tyr Tyr Asn Asn Pro Ser Tyr Thr Phe Val Val
            85                  90                  95

Ser Asn Thr Ala Phe Asn Arg Ser Val Thr Phe Asn Ser Ala Thr Gly
            100                 105                 110

Gly Val Asp Val Asn Val Trp
        115
```

<210> SEQ ID NO 4
<211> LENGTH: 182
<212> TYPE: PRT
<213> ORGANISM: Desulfurvibrio alkaliphilus

```
<400> SEQUENCE: 4

Phe Thr Leu Val Glu Leu Met Ile Val Ala Ile Ile Gly Ile Leu
1               5                   10                  15

Ala Ala Val Ala Ile Pro Gln Phe Ala Gln Tyr Arg Ile Arg Gly Phe
                20                  25                  30

Asn Ser Ser Ala Leu Ser Asp Val Arg Asn Leu Thr Thr Ala Gln Glu
            35                  40                  45

Ala Phe Phe Ala Asp Trp Leu Arg Tyr Ala Val Thr His Glu Ala Ala
        50                  55                  60

Asp Val Thr Glu Val Lys Ala Thr Gly Asp Leu Leu Glu Gly Pro Ser
65                  70                  75                  80

Thr Gly Ala Met Val Leu Ala Gln Trp Ala Arg Gln Ala His Gln Gln
                85                  90                  95

Leu Pro Leu Ala Ile Gly Asn Gly Val Val Met Gln Ala Asp Val Ile
            100                 105                 110

Pro Ala Thr Ala Val Ser Tyr Val Ala Ile Ser Lys His Leu Gln Gly
        115                 120                 125

Asn Thr Met Tyr Gly Ala Thr Asn Thr Ser Thr Ala Ile His Arg Asp
130                 135                 140

Gln Glu Thr Leu Val Pro Gly Gln Gly Gly Asp Val Leu Pro Ile Thr
145                 150                 155                 160

Gly Tyr Met Pro Glu Pro His Glu Thr Asp Asp Pro Phe Ile Asp His
                165                 170                 175

Glu Glu Phe Glu Ala Gln
            180

<210> SEQ ID NO 5
<211> LENGTH: 60
<212> TYPE: PRT
<213> ORGANISM: Felxistipes sinusarabici

<400> SEQUENCE: 5

Phe Thr Leu Ile Glu Leu Leu Val Val Ala Ile Ile Gly Ile Leu
1               5                   10                  15

Ala Ala Ile Ala Ile Pro Gln Phe Ala Lys Tyr Arg Ile Asn Ala Phe
                20                  25                  30

Asn Ser Ala Ala Gln Ser Asp Leu Ala Asn Val Lys Ser Ala Leu Glu
            35                  40                  45

Ser Tyr Tyr Ala Glu Asn Phe Thr Tyr Pro Ser Pro
        50                  55                  60

<210> SEQ ID NO 6
<211> LENGTH: 110
<212> TYPE: PRT
<213> ORGANISM: Synthrophus aciditrophicus

<400> SEQUENCE: 6

Phe Thr Leu Ile Glu Leu Met Ile Val Ala Ile Ile Gly Ile Leu
1               5                   10                  15

Ala Ala Ile Ala Ile Pro Gln Phe Gln Gln Tyr Arg Thr Arg Gly Tyr
                20                  25                  30

Asn Thr Ala Ala Lys Ala Asp Ala Lys Asn Ala Tyr Thr Ala Ala Gln
            35                  40                  45

Ala Tyr Phe Ser Asp His Pro Ser Val Thr Ile Ser Ser Ile Thr Asp
        50                  55                  60
```

```
Leu Ala Asn Tyr Gly Phe Lys Ala Ser Ala Asp Val Thr Thr Ala
 65                  70                  75                  80

Ala Gly Asp Met Asp Gly Leu Ala Ile Thr Ala Lys His Ser Ala Ser
                 85                  90                  95

Asp Thr Thr Tyr Gln Val Asp Ser Gln Gly Thr Ile Thr Pro
            100                 105                 110

<210> SEQ ID NO 7
<211> LENGTH: 120
<212> TYPE: PRT
<213> ORGANISM: Syntrophus gentianae

<400> SEQUENCE: 7

Phe Thr Leu Ile Glu Leu Met Ile Val Ile Ala Ile Gly Ile Leu
  1               5                  10                  15

Ala Ala Ile Ala Ile Pro Gln Phe Thr Gln Tyr Arg Lys Arg Ala Tyr
                 20                  25                  30

Asp Ala Ser Ser Lys Ala Asp Leu Lys Ser Ala Tyr Thr Ala Ala Gln
            35                  40                  45

Ala Trp Phe Asn Asp Asn Pro Ser Gly Thr Leu Pro Ala Ala Thr Ile
 50                  55                  60

Thr Ser Ala Thr Thr Thr Gly Glu Leu Pro Gly Asn Gly Phe Lys Ala
 65                  70                  75                  80

Ser Thr Gly Val Thr Ala Thr Val Thr Ser Gly Thr Met Gly Thr Phe
                 85                  90                  95

Ser Ile Ala Thr Thr His Ser Gln Gly Thr Lys Thr Tyr Asn Ile Thr
            100                 105                 110

Ala Gly Gly Thr Leu Thr Glu Ser
        115                 120

<210> SEQ ID NO 8
<211> LENGTH: 109
<212> TYPE: PRT
<213> ORGANISM: Smithella sp. F21

<400> SEQUENCE: 8

Phe Thr Leu Ile Glu Leu Met Ile Val Val Ala Ile Ile Gly Ile Leu
  1               5                  10                  15

Ala Ala Ile Ala Ile Pro Gln Phe Ala Asn Tyr Arg Thr Lys Gly Tyr
                 20                  25                  30

Asn Thr Lys Ala Lys Ala Glu Leu Lys Ser Ala Tyr Thr Ala Cys Gln
            35                  40                  45

Ala Tyr Phe Ser Asp Asn Pro Gly Ala Thr Ala Cys Ala Asn Ala Thr
 50                  55                  60

Leu Gly Gly Phe Asn Asn Ser Ser Asp Val Asn Ile Ala Val Gly Leu
 65                  70                  75                  80

Ser Thr Pro Thr Gly Trp Thr Ala Thr Ala Ser His Ile Gly Gly Asn
                 85                  90                  95

Gln Thr Phe Thr Val Asp Asn Gly Gly Arg Ile Thr Pro
            100                 105

<210> SEQ ID NO 9
<211> LENGTH: 141
<212> TYPE: PRT
<213> ORGANISM: Syntrophobacter fumaroxidans

<400> SEQUENCE: 9

Phe Thr Leu Val Glu Leu Met Ile Val Val Ala Ile Ile Gly Ile Leu
```

```
                1               5                  10                 15
        Ala Ala Val Ala Val Pro Tyr Tyr Gln Lys Tyr Ile Gln Lys Ser Arg
                        20                  25                 30

Met Val Ser Lys Val Phe Pro Gly Met His Ala Ile Glu Thr Asn Met
                        35                  40                 45

Gly Thr Tyr Phe Ser Phe Lys Asn Thr Leu Leu Asp Val Gly Ser Thr
                        50                  55                 60

Ala Thr Phe Gly Gln Phe Val Gln Asp Ala Asp Thr Lys Cys Phe Ser
        65                      70                  75                 80

Pro Ser Trp Ala Gly Glu Tyr Leu Leu Ile Thr Ile Lys Asp Pro Thr
                        85                  90                 95

Leu Cys Gln Glu Leu Lys Ala Leu Thr Gly Met Thr Leu Ser Ala Thr
                        100                 105                110

Pro Arg Met Asp Thr Ser Arg Thr Lys Ile Arg Gly Trp Ala Leu Ala
                        115                 120                125

Gly Pro Leu Ala Val Gln Leu Gly Leu Glu Gly Glu Gln
                        130                 135                140
```

<210> SEQ ID NO 10
<211> LENGTH: 159
<212> TYPE: PRT
<213> ORGANISM: Syntrophobacter sp. DG_60

<400> SEQUENCE: 10

```
        Phe Thr Leu Ile Glu Leu Met Ile Val Val Ala Ile Ile Ala Ile Leu
        1               5                  10                 15

Ala Ala Ile Ala Ile Pro Gln Tyr Lys Lys Phe Gln Leu Lys Ala Lys
                        20                  25                 30

Thr Ser Glu Ala Lys Ala Asn Leu Gly Ser Ile Arg Ser Cys Glu Glu
                        35                  40                 45

Ala Tyr Ser Ala Glu Thr Asp Asn Tyr Val Phe Cys Gly Trp Thr Pro
                        50                  55                 60

Ser Asn Ala Pro Thr Ala Ala Gly Gln Ala Trp Val Thr Thr Ser Gly
        65                      70                  75                 80

His Glu Gly Phe Val Ser Ile Gly Phe Ala Pro Ala Gly Thr Ser Arg
                        85                  90                 95

Tyr Cys Tyr Cys Val Gly Gly Ser Val Asn Thr Ala Gly Thr Asp Ala
                        100                 105                110

Ala Thr Asn Ala Phe Asn Glu Gly Asn Val Asp Ile Tyr Met Thr Ala
                        115                 120                125

Lys Gly Asp Leu Asp Gly Asp Gly Ser Asn Gln Trp Phe Tyr Ala Thr
                        130                 135                140

Asp Glu Asp Leu Lys Val Met Ala Asp Tyr Ser Gln Asp Asp Phe
        145                     150                 155
```

<210> SEQ ID NO 11
<211> LENGTH: 145
<212> TYPE: PRT
<213> ORGANISM: Syntrophobacter sp. SbD1

<400> SEQUENCE: 11

```
        Phe Thr Leu Val Glu Leu Met Ile Val Val Ala Ile Ile Gly Ile Leu
        1               5                  10                 15

Ala Ala Val Ala Val Pro Tyr Tyr Gln Lys Tyr Ile Gln Lys Ala Arg
                        20                  25                 30

Leu Thr Ser Lys Val Ile Pro Gly Ile His Ser Ile Gln Thr Asp Leu
```

```
            35                  40                  45
Ala Thr Tyr Phe Ser Phe Gln Gln Met Phe Pro Gly Ala Gly Ala Thr
        50                  55                  60

Val Asn Ala Met Phe Thr Asp Ala Asn Thr His Cys Phe Thr Pro Thr
 65                  70                  75                  80

Val Thr Ser Ala Ala Gly Ala Thr Ser Asn Phe Lys Ile Thr Phe Ala
                85                  90                  95

Ile Val Gly Ala Gly Cys Thr Glu Leu Ser Ser Leu Tyr Asn Gln Thr
            100                 105                 110

Ile Thr Ala Ser Pro Ile Leu Gly Asn Asn Ala Gln Val Ile Thr Gly
        115                 120                 125

Trp Thr Phe Gly Gly Thr Leu Ala Ala Asn Met Gly Leu Ala Gly Ala
        130                 135                 140

Gln
145

<210> SEQ ID NO 12
<211> LENGTH: 128
<212> TYPE: PRT
<213> ORGANISM: Syntrophorhabdus aromaticivorans

<400> SEQUENCE: 12

Phe Thr Leu Ile Glu Leu Leu Ile Val Ile Ala Ile Ile Gly Val Leu
 1               5                  10                  15

Ala Ala Ile Ala Ile Pro Ala Tyr Thr Gly Tyr Thr Lys Lys Ala Lys
                20                  25                  30

Val Gly Glu Ile Ile His Ala Leu Gly Ala Ile Lys Ser Ala Val Ser
            35                  40                  45

Val Tyr Tyr Ser Glu Ala Gly Ala Thr Thr Asp Ala Thr Thr Ala Asp
        50                  55                  60

Leu Ile Arg Thr Thr Tyr Gly Val Asp Val Pro Thr Gly Arg Ala Ser
 65                  70                  75                  80

Phe Gln Tyr Thr Ala Thr Ser Arg Glu Ile Gln Ala Thr Ser Lys Ile
                85                  90                  95

Thr Gly Val Thr Gly Thr Met Thr Leu Thr Gly Ser Thr Asp Phe Lys
            100                 105                 110

Thr Trp Thr Trp Asp Gly Thr Met Asp Lys Ala Tyr Ile Pro Lys Asn
        115                 120                 125

<210> SEQ ID NO 13
<211> LENGTH: 114
<212> TYPE: PRT
<213> ORGANISM: Desulfatibacillum alkenivorans PilA

<400> SEQUENCE: 13

Phe Thr Leu Ile Glu Leu Met Ile Val Ile Ala Ile Ile Gly Ile Leu
 1               5                  10                  15

Ala Ala Ile Ala Ile Pro Asn Phe Val Ser Tyr Arg Lys Lys Ala Tyr
                20                  25                  30

Asn Arg Thr Ala Gln Ala Asp Leu Ser Ser Ala Tyr Ser Thr Val Met
            35                  40                  45

Ala Tyr Tyr Ala Asp Glu Lys His Lys Glu Ile Asp Asn Phe Thr Leu
        50                  55                  60

Asp Asn Leu Lys Asp Ala Gly Phe Lys Gln Thr Val Gly Val Ala Val
 65                  70                  75                  80

Thr Val Thr Ser Val Asn Phe Gln Asp Phe Glu Leu Thr Ala Arg His
```

85                  90                  95

Ser Gln Gly Asp Ile Val Tyr Thr Ile Asp Ala Ala Gly Ala Arg Ser
                100                 105                 110

His Asn

<210> SEQ ID NO 14
<211> LENGTH: 157
<212> TYPE: PRT
<213> ORGANISM: Syntrophomonas zehnderi PilA

<400> SEQUENCE: 14

Phe Thr Leu Ile Glu Ile Leu Val Ala Leu Phe Leu Ala Ile Leu Val
1               5                   10                  15

Ala Ser Ser Leu Val Thr Val Phe Gln Met Ser His His Ile Phe Tyr
                20                  25                  30

Arg Asp Phe Ser Arg Ser Glu Leu Gln Tyr Met Ala Arg Lys Ala Met
            35                  40                  45

Glu Asp Ile Ile Asp Tyr Val Val Gln Ala Gln Pro Asp Ser Leu Ala
        50                  55                  60

Val Asn Gly Ala Glu Gly Ser Gln Leu Glu Phe Ile Leu Ser Ser Gly
65                  70                  75                  80

Ala Lys Ile Gln Tyr Ser Gln Gly Ala Asn Tyr Trp Leu Tyr Arg Lys
                85                  90                  95

Gly Pro Asp Ser Gly Pro Pro Gln Pro Ile Val Glu Gln Ile Ala Lys
                100                 105                 110

Val Lys Phe Cys Leu Ser Gly Pro His Ile Leu Thr Val Asp Val Val
            115                 120                 125

Ala Gly Asn Glu Lys Asn Ser Phe Thr Leu Thr Gln Met Ile Val Pro
        130                 135                 140

Arg Ala Glu Ile Asp Glu Asn Asp Trp Leu Asn Ser Leu
145                 150                 155

<210> SEQ ID NO 15
<211> LENGTH: 105
<212> TYPE: PRT
<213> ORGANISM: Syntrophaceticus schinkii PilA

<400> SEQUENCE: 15

Phe Thr Leu Val Glu Leu Met Val Leu Leu Ile Ile Gly Ile Leu
1               5                   10                  15

Val Ala Ile Ala Ile Pro Ile Tyr Asn Lys Thr Gln Glu Asn Ala Gln
                20                  25                  30

Lys Arg Ala Cys Gln Ser Asn Leu Arg Thr Leu Asp Ser Ala Ala Ala
            35                  40                  45

Gln Tyr Gly Ala Ala Thr Gly Asn Tyr Pro Thr Asp Pro Leu Asn Asn
        50                  55                  60

Ala Asn Phe Val Gly Glu Asn Gly Tyr Val Lys Thr Lys Pro Thr Cys
65                  70                  75                  80

Pro Ala Gly Gly Val Tyr Asn Tyr Asp Ala Thr Asn Gly Lys Phe Ser
                85                  90                  95

Cys Asn Val Pro Asp His Val Tyr Pro
                100                 105

<210> SEQ ID NO 16
<211> LENGTH: 144
<212> TYPE: PRT
<213> ORGANISM: Tepidanaerobacter acetatoxydans PilA -continued

<400> SEQUENCE: 16

Phe Thr Leu Ile Glu Leu Ile Leu Ala Leu Gly Leu Ser Leu Ile
1               5                   10                  15

Met Thr Thr Ser Phe Thr Ile Tyr Ser Ala Gly Gln Lys Thr Tyr Glu
            20                  25                  30

Tyr Glu Asn Ser Lys Ile Phe Val Gln Gln Asn Ala Arg Gln Ala Phe
        35                  40                  45

Leu Trp Leu Ser Thr Ser Ile Lys Gln Ala Arg Ser Val Glu Val Met
50                  55                  60

Ser Glu Asn Ser Ile Lys Thr Val Ala Gly Asp Gly Glu Thr Ile Ile
65                  70                  75                  80

Tyr Tyr Phe Lys Asn Gly Val Leu Tyr Arg Glu Lys Asn Asn Gly Ile
                85                  90                  95

Asn Pro Ile Ala Glu Leu Ser Gln Leu Lys Phe Lys Gln Pro Lys Asp
            100                 105                 110

Lys Gln Tyr Ile Glu Ile Phe Leu Ala Ala Gln Gly Lys Glu Gly Asp
        115                 120                 125

Asp Ile Ile Ile Lys Thr Lys Ala Thr Pro Phe Gly Leu Trp Val Asn
130                 135                 140

<210> SEQ ID NO 17
<211> LENGTH: 128
<212> TYPE: PRT
<213> ORGANISM: Thermacetogenium phaeum PilA

<400> SEQUENCE: 17

Phe Thr Met Ile Glu Met Met Val Val Leu Ile Ile Ile Ala Val Leu
1               5                   10                  15

Ile Ala Gly Gly Ile Arg Phe Tyr Leu Gly Tyr Val Glu Arg Ala Lys
            20                  25                  30

Val Thr Lys Ala Lys Ser Glu Ile Thr Thr Met Gln Ala Ala Leu Asp
        35                  40                  45

Ser Tyr Tyr Ala Glu Lys Gly Glu Tyr Pro Asp Asp Glu Asn Asp Arg
50                  55                  60

Glu Leu Val Lys Ala Gly Leu Ala Thr Asp Arg Ile Ser Ile Ser Thr
65                  70                  75                  80

Glu Gly Asn Asp Ser Ile Gln Tyr Ile Tyr Glu Gly Gly Asn Ser
                85                  90                  95

Tyr Lys Ile Ile Thr Thr Ala Thr Phe Arg Ala Gly Lys Leu Val Gly
            100                 105                 110

Glu Gly Gln Asp Gly Lys Ser Thr Glu Pro Asp Phe Gly Ser Gly Glu
        115                 120                 125

<210> SEQ ID NO 18
<211> LENGTH: 59
<212> TYPE: PRT
<213> ORGANISM: Geobacter metallireducens

<400> SEQUENCE: 18

Phe Thr Leu Ile Glu Leu Leu Ile Val Val Ala Ile Ile Gly Ile Leu
1               5                   10                  15

Ala Ala Ile Ala Ile Pro Gln Phe Ala Ala Tyr Arg Gln Lys Ala Phe
            20                  25                  30

Asn Ser Ala Ala Glu Ser Asp Leu Lys Asn Thr Lys Thr Asn Leu Glu
        35                  40                  45

```
Ser Tyr Tyr Ser Glu His Gln Phe Tyr Pro Asn
    50                  55
```

<210> SEQ ID NO 19
<211> LENGTH: 119
<212> TYPE: PRT
<213> ORGANISM: Calditerrivibrio nitroreducens

<400> SEQUENCE: 19

```
Phe Thr Leu Ile Glu Leu Leu Val Val Ala Ile Ile Ala Ile Leu
1               5                   10                  15

Ala Ala Ile Ala Ile Pro Gln Phe Ala Lys Tyr Arg Glu Asn Ala Ala
                20                  25                  30

Lys Ala Ser Ala Val Ala Asp Ala Lys Asn Ile Ala Thr Ala Ile Glu
            35                  40                  45

Ser Tyr Tyr Ala Asp Thr Gln Ser Phe Pro Ser Ser Ile Ser Asp Gly
    50                  55                  60

Ser Ile Val Pro Leu Gly Thr Gln Thr Phe Ser Leu Ser Lys Asn Asn
65                  70                  75                  80

Ser Phe Lys Gly Tyr Tyr Tyr Asn Asn Pro Ser Tyr Thr Phe Val Val
                85                  90                  95

Ser Asn Thr Ala Phe Asn Arg Ser Val Thr Phe Asn Ser Ala Thr Gly
            100                 105                 110

Gly Val Asp Val Asn Val Trp
        115
```

<210> SEQ ID NO 20
<211> LENGTH: 182
<212> TYPE: PRT
<213> ORGANISM: Desulfurvibrio alkaliphilus

<400> SEQUENCE: 20

```
Phe Thr Leu Val Glu Leu Met Ile Val Ala Ile Ile Gly Ile Leu
1               5                   10                  15

Ala Ala Val Ala Ile Pro Gln Phe Ala Gln Tyr Arg Ile Arg Gly Phe
                20                  25                  30

Asn Ser Ser Ala Leu Ser Asp Val Arg Asn Leu Thr Thr Ala Gln Glu
            35                  40                  45

Ala Phe Phe Ala Asp Trp Leu Arg Tyr Ala Val Thr His Glu Ala Ala
    50                  55                  60

Asp Val Thr Glu Val Lys Ala Thr Gly Asp Leu Leu Glu Gly Pro Ser
65                  70                  75                  80

Thr Gly Ala Met Val Leu Ala Gln Trp Ala Arg Gln Ala His Gln Gln
                85                  90                  95

Leu Pro Leu Ala Ile Gly Asn Gly Val Val Met Gln Ala Asp Val Ile
            100                 105                 110

Pro Ala Thr Ala Val Ser Tyr Val Ala Ile Ser Lys His Leu Gln Gly
        115                 120                 125

Asn Thr Met Tyr Gly Ala Thr Asn Thr Ser Thr Ala Ile His Arg Asp
    130                 135                 140

Gln Glu Thr Leu Val Pro Gly Gln Gly Gly Asp Val Leu Pro Ile Thr
145                 150                 155                 160

Gly Tyr Met Pro Glu Pro His Glu Thr Asp Asp Pro Phe Ile Asp His
                165                 170                 175

Glu Glu Phe Glu Ala Gln
            180
```

<210> SEQ ID NO 21
<211> LENGTH: 60
<212> TYPE: PRT
<213> ORGANISM: Felxistipes sinusarabici

<400> SEQUENCE: 21

Phe Thr Leu Ile Glu Leu Leu Val Val Ala Ile Ile Gly Ile Leu
1               5                   10                  15

Ala Ala Ile Ala Ile Pro Gln Phe Ala Lys Tyr Arg Ile Asn Ala Phe
            20                  25                  30

Asn Ser Ala Ala Gln Ser Asp Leu Ala Asn Val Lys Ser Ala Leu Glu
        35                  40                  45

Ser Tyr Tyr Ala Glu Asn Phe Thr Tyr Pro Ser Pro
    50                  55                  60

<210> SEQ ID NO 22
<211> LENGTH: 110
<212> TYPE: PRT
<213> ORGANISM: Synthrophus aciditrophicus

<400> SEQUENCE: 22

Phe Thr Leu Ile Glu Leu Met Ile Val Ile Ala Ile Ile Gly Ile Leu
1               5                   10                  15

Ala Ala Ile Ala Ile Pro Gln Phe Gln Gln Tyr Arg Thr Arg Gly Tyr
            20                  25                  30

Asn Thr Ala Ala Lys Ala Asp Ala Lys Asn Ala Tyr Thr Ala Ala Gln
        35                  40                  45

Ala Tyr Phe Ser Asp His Pro Ser Val Thr Ile Ser Ser Ile Thr Asp
    50                  55                  60

Leu Ala Asn Tyr Gly Phe Lys Ala Ser Ala Asp Val Thr Thr Thr Ala
65                  70                  75                  80

Ala Gly Asp Met Asp Gly Leu Ala Ile Thr Ala Lys His Ser Ala Ser
                85                  90                  95

Asp Thr Thr Tyr Gln Val Asp Ser Gln Gly Thr Ile Thr Pro
            100                 105                 110

<210> SEQ ID NO 23
<211> LENGTH: 120
<212> TYPE: PRT
<213> ORGANISM: Syntrophus gentianae

<400> SEQUENCE: 23

Phe Thr Leu Ile Glu Leu Met Ile Val Ile Ala Ile Ile Gly Ile Leu
1               5                   10                  15

Ala Ala Ile Ala Ile Pro Gln Phe Thr Gln Tyr Arg Lys Arg Ala Tyr
            20                  25                  30

Asp Ala Ser Ser Lys Ala Asp Leu Lys Ser Ala Tyr Thr Ala Ala Gln
        35                  40                  45

Ala Trp Phe Asn Asp Asn Pro Ser Gly Thr Leu Pro Ala Ala Thr Ile
    50                  55                  60

Thr Ser Ala Thr Thr Thr Gly Glu Leu Pro Gly Asn Gly Phe Lys Ala
65                  70                  75                  80

Ser Thr Gly Val Thr Ala Thr Val Thr Ser Gly Thr Met Gly Thr Phe
                85                  90                  95

Ser Ile Ala Thr Thr His Ser Gln Gly Thr Lys Thr Tyr Asn Ile Thr
            100                 105                 110

Ala Gly Gly Thr Leu Thr Glu Ser

```
                115                 120
```

<210> SEQ ID NO 24
<211> LENGTH: 109
<212> TYPE: PRT
<213> ORGANISM: Smithella sp. F21

<400> SEQUENCE: 24

```
Phe Thr Leu Ile Glu Leu Met Ile Val Val Ala Ile Ile Gly Ile Leu
1               5                   10                  15

Ala Ala Ile Ala Ile Pro Gln Phe Ala Asn Tyr Arg Thr Lys Gly Tyr
            20                  25                  30

Asn Thr Lys Ala Lys Ala Glu Leu Lys Ser Ala Tyr Thr Ala Cys Gln
        35                  40                  45

Ala Tyr Phe Ser Asp Asn Pro Gly Ala Thr Ala Cys Ala Asn Ala Thr
    50                  55                  60

Leu Gly Gly Phe Asn Asn Ser Ser Asp Val Asn Ile Ala Val Gly Leu
65                  70                  75                  80

Ser Thr Pro Thr Gly Trp Thr Ala Thr Ala Ser His Ile Gly Gly Asn
                85                  90                  95

Gln Thr Phe Thr Val Asp Asn Gly Gly Arg Ile Thr Pro
            100                 105
```

<210> SEQ ID NO 25
<211> LENGTH: 141
<212> TYPE: PRT
<213> ORGANISM: Syntrophobacter fumaroxidans

<400> SEQUENCE: 25

```
Phe Thr Leu Val Glu Leu Met Ile Val Val Ala Ile Ile Gly Ile Leu
1               5                   10                  15

Ala Ala Val Ala Val Pro Tyr Tyr Gln Lys Tyr Ile Gln Lys Ser Arg
            20                  25                  30

Met Val Ser Lys Val Phe Pro Gly Met His Ala Ile Glu Thr Asn Met
        35                  40                  45

Gly Thr Tyr Phe Ser Phe Lys Asn Thr Leu Leu Asp Val Gly Ser Thr
    50                  55                  60

Ala Thr Phe Gly Gln Phe Val Gln Asp Ala Asp Thr Lys Cys Phe Ser
65                  70                  75                  80

Pro Ser Trp Ala Gly Glu Tyr Leu Leu Ile Thr Ile Lys Asp Pro Thr
                85                  90                  95

Leu Cys Gln Glu Leu Lys Ala Leu Thr Gly Met Thr Leu Ser Ala Thr
            100                 105                 110

Pro Arg Met Asp Thr Ser Arg Thr Lys Ile Arg Gly Trp Ala Leu Ala
        115                 120                 125

Gly Pro Leu Ala Val Gln Leu Gly Leu Glu Gly Glu Gln
    130                 135                 140
```

<210> SEQ ID NO 26
<211> LENGTH: 159
<212> TYPE: PRT
<213> ORGANISM: Syntrophobacter sp. DG_60

<400> SEQUENCE: 26

```
Phe Thr Leu Ile Glu Leu Met Ile Val Val Ala Ile Ile Ala Ile Leu
1               5                   10                  15

Ala Ala Ile Ala Ile Pro Gln Tyr Lys Lys Phe Gln Leu Lys Ala Lys
            20                  25                  30
```

```
Thr Ser Glu Ala Lys Ala Asn Leu Gly Ser Ile Arg Ser Cys Glu Glu
        35                  40                  45

Ala Tyr Ser Ala Glu Thr Asp Asn Tyr Val Phe Cys Gly Trp Thr Pro
    50                  55                  60

Ser Asn Ala Pro Thr Ala Ala Gly Gln Ala Trp Val Thr Thr Ser Gly
65                  70                  75                  80

His Glu Gly Phe Val Ser Ile Gly Phe Ala Pro Ala Gly Thr Ser Arg
                85                  90                  95

Tyr Cys Tyr Cys Val Gly Gly Ser Val Asn Thr Ala Gly Thr Asp Ala
            100                 105                 110

Ala Thr Asn Ala Phe Asn Glu Gly Asn Val Asp Ile Tyr Met Thr Ala
                115                 120                 125

Lys Gly Asp Leu Asp Gly Asp Gly Ser Asn Gln Trp Phe Tyr Ala Thr
    130                 135                 140

Asp Glu Asp Leu Lys Val Met Ala Asp Tyr Ser Gln Asp Asp Phe
145                 150                 155

<210> SEQ ID NO 27
<211> LENGTH: 145
<212> TYPE: PRT
<213> ORGANISM: Syntrophobacter sp. SbD1

<400> SEQUENCE: 27

Phe Thr Leu Val Glu Leu Met Ile Val Val Ala Ile Ile Gly Ile Leu
1               5                   10                  15

Ala Ala Val Ala Val Pro Tyr Tyr Gln Lys Tyr Ile Gln Lys Ala Arg
            20                  25                  30

Leu Thr Ser Lys Val Ile Pro Gly Ile His Ser Ile Gln Thr Asp Leu
        35                  40                  45

Ala Thr Tyr Phe Ser Phe Gln Gln Met Phe Pro Gly Ala Gly Ala Thr
    50                  55                  60

Val Asn Ala Met Phe Thr Asp Ala Asn Thr His Cys Phe Thr Pro Thr
65                  70                  75                  80

Val Thr Ser Ala Ala Gly Ala Thr Ser Asn Phe Lys Ile Thr Phe Ala
                85                  90                  95

Ile Val Gly Ala Gly Cys Thr Glu Leu Ser Ser Leu Tyr Asn Gln Thr
            100                 105                 110

Ile Thr Ala Ser Pro Ile Leu Gly Asn Asn Ala Gln Val Ile Thr Gly
        115                 120                 125

Trp Thr Phe Gly Gly Thr Leu Ala Ala Asn Met Gly Leu Ala Gly Ala
    130                 135                 140

Gln
145

<210> SEQ ID NO 28
<211> LENGTH: 128
<212> TYPE: PRT
<213> ORGANISM: Syntrophorhabdus aromaticivorans

<400> SEQUENCE: 28

Phe Thr Leu Ile Glu Leu Leu Ile Val Ile Ala Ile Ile Gly Val Leu
1               5                   10                  15

Ala Ala Ile Ala Ile Pro Ala Tyr Thr Gly Tyr Thr Lys Lys Ala Lys
            20                  25                  30

Val Gly Glu Ile Ile His Ala Leu Gly Ala Ile Lys Ser Ala Val Ser
        35                  40                  45
```

```
Val Tyr Tyr Ser Glu Ala Gly Ala Thr Thr Asp Ala Thr Ala Asp
     50                  55                  60

Leu Ile Arg Thr Thr Tyr Gly Val Asp Val Pro Thr Gly Arg Ala Ser
 65                  70                  75                  80

Phe Gln Tyr Thr Ala Thr Ser Arg Glu Ile Gln Ala Thr Ser Lys Ile
                 85                  90                  95

Thr Gly Val Thr Gly Thr Met Thr Leu Thr Gly Ser Thr Asp Phe Lys
                100                 105                 110

Thr Trp Thr Trp Asp Gly Thr Met Asp Lys Ala Tyr Ile Pro Lys Asn
                115                 120                 125
```

<210> SEQ ID NO 29
<211> LENGTH: 114
<212> TYPE: PRT
<213> ORGANISM: Desulfatibacillum alkenivorans PilA

<400> SEQUENCE: 29

```
Phe Thr Leu Ile Glu Leu Met Ile Val Ile Ala Ile Gly Ile Leu
 1               5                  10                  15

Ala Ala Ile Ala Ile Pro Asn Phe Val Ser Tyr Arg Lys Lys Ala Tyr
                 20                  25                  30

Asn Arg Thr Ala Gln Ala Asp Leu Ser Ser Ala Tyr Ser Thr Val Met
             35                  40                  45

Ala Tyr Tyr Ala Asp Glu Lys His Lys Glu Ile Asp Asn Phe Thr Leu
 50                  55                  60

Asp Asn Leu Lys Asp Ala Gly Phe Lys Gln Thr Val Gly Val Ala Val
 65                  70                  75                  80

Thr Val Thr Ser Val Asn Phe Gln Asp Phe Glu Leu Thr Ala Arg His
                 85                  90                  95

Ser Gln Gly Asp Ile Val Tyr Thr Ile Asp Ala Ala Gly Ala Arg Ser
                100                 105                 110

His Asn
```

<210> SEQ ID NO 30
<211> LENGTH: 157
<212> TYPE: PRT
<213> ORGANISM: Syntrophomonas zehnderi PilA

<400> SEQUENCE: 30

```
Phe Thr Leu Ile Glu Ile Leu Val Ala Leu Phe Leu Ala Ile Leu Val
 1               5                  10                  15

Ala Ser Ser Leu Val Thr Val Phe Gln Met Ser His His Ile Phe Tyr
                 20                  25                  30

Arg Asp Phe Ser Arg Ser Glu Leu Gln Tyr Met Ala Arg Lys Ala Met
             35                  40                  45

Glu Asp Ile Ile Asp Tyr Val Val Gln Ala Gln Pro Asp Ser Leu Ala
 50                  55                  60

Val Asn Gly Ala Glu Gly Ser Gln Leu Glu Phe Ile Leu Ser Ser Gly
 65                  70                  75                  80

Ala Lys Ile Gln Tyr Ser Gln Gly Ala Asn Tyr Trp Leu Tyr Arg Lys
                 85                  90                  95

Gly Pro Asp Ser Gly Pro Gln Pro Ile Val Glu Gln Ile Ala Lys
                100                 105                 110

Val Lys Phe Cys Leu Ser Gly Pro His Ile Leu Thr Val Asp Val Val
            115                 120                 125
```

```
Ala Gly Asn Glu Lys Asn Ser Phe Thr Leu Thr Gln Met Ile Val Pro
            130                 135                 140

Arg Ala Glu Ile Asp Glu Asn Asp Trp Leu Asn Ser Leu
145                 150                 155
```

<210> SEQ ID NO 31
<211> LENGTH: 105
<212> TYPE: PRT
<213> ORGANISM: Syntrophaceticus schinkii PilA

<400> SEQUENCE: 31

```
Phe Thr Leu Val Glu Leu Met Val Val Leu Ile Ile Gly Ile Leu
1               5                   10                  15

Val Ala Ile Ala Ile Pro Ile Tyr Asn Lys Thr Gln Glu Asn Ala Gln
                20                  25                  30

Lys Arg Ala Cys Gln Ser Asn Leu Arg Thr Leu Asp Ser Ala Ala Ala
                35                  40                  45

Gln Tyr Gly Ala Ala Thr Gly Asn Tyr Pro Thr Asp Pro Leu Asn Asn
50                  55                  60

Ala Asn Phe Val Gly Glu Asn Gly Tyr Val Lys Thr Lys Pro Thr Cys
65                  70                  75                  80

Pro Ala Gly Gly Val Tyr Asn Tyr Asp Ala Thr Asn Gly Lys Phe Ser
                85                  90                  95

Cys Asn Val Pro Asp His Val Tyr Pro
                100                 105
```

<210> SEQ ID NO 32
<211> LENGTH: 144
<212> TYPE: PRT
<213> ORGANISM: Tepidanaerobacter acetatoxydans PilA

<400> SEQUENCE: 32

```
Phe Thr Leu Ile Glu Leu Ile Leu Ala Leu Gly Leu Leu Ser Leu Ile
1               5                   10                  15

Met Thr Thr Ser Phe Thr Ile Tyr Ser Ala Gly Gln Lys Thr Tyr Glu
                20                  25                  30

Tyr Glu Asn Ser Lys Ile Phe Val Gln Gln Asn Ala Arg Gln Ala Phe
                35                  40                  45

Leu Trp Leu Ser Thr Ser Ile Lys Gln Ala Arg Ser Val Glu Val Met
50                  55                  60

Ser Glu Asn Ser Ile Lys Thr Val Ala Gly Asp Gly Glu Thr Ile Ile
65                  70                  75                  80

Tyr Tyr Phe Lys Asn Gly Val Leu Tyr Arg Glu Lys Asn Asn Gly Ile
                85                  90                  95

Asn Pro Ile Ala Glu Leu Ser Gln Leu Lys Phe Lys Gln Pro Lys Asp
                100                 105                 110

Lys Gln Tyr Ile Glu Ile Phe Leu Ala Ala Gln Gly Lys Glu Gly Asp
            115                 120                 125

Asp Ile Ile Ile Lys Thr Lys Ala Thr Pro Phe Gly Leu Trp Val Asn
            130                 135                 140
```

<210> SEQ ID NO 33
<211> LENGTH: 128
<212> TYPE: PRT
<213> ORGANISM: Thermacetogenium phaeum PilA

<400> SEQUENCE: 33

```
Phe Thr Met Ile Glu Met Met Val Val Leu Ile Ile Ile Ala Val Leu
```

-continued

```
1               5                   10                  15

Ile Ala Gly Gly Ile Arg Phe Tyr Leu Gly Tyr Val Glu Arg Ala Lys
            20                  25                  30

Val Thr Lys Ala Lys Ser Glu Ile Thr Thr Met Gln Ala Ala Leu Asp
            35                  40                  45

Ser Tyr Tyr Ala Glu Lys Gly Glu Tyr Pro Asp Asp Glu Asn Asp Arg
        50                  55                  60

Glu Leu Val Lys Ala Gly Leu Ala Thr Asp Arg Ile Ser Ile Ser Thr
65                  70                  75                  80

Glu Gly Asn Asp Ser Ile Gln Tyr Ile Tyr Glu Gly Gly Gly Asn Ser
                85                  90                  95

Tyr Lys Ile Ile Thr Thr Ala Thr Phe Arg Ala Gly Lys Leu Val Gly
            100                 105                 110

Glu Gly Gln Asp Gly Lys Ser Thr Glu Pro Asp Phe Gly Ser Gly Glu
            115                 120                 125
```

SENSORS COMPRISING ELECTRICALLY-CONDUCTIVE PROTEIN NANOWIRES

RELATED APPLICATION(S)

This application claims the benefit of U.S. Provisional Application No. 63/014,043, filed on Apr. 22, 2020. The entire teachings of the above application are incorporated herein by reference.

GOVERNMENT SUPPORT

This invention was made with government support under Grant No. 1917630 awarded by the National Science Foundation. The government has certain rights in the invention.

INCORPORATION BY REFERENCE OF MATERIAL IN ASCII TEXT FILE

This application incorporates by reference the Sequence Listing contained in the following ASCII text file:

a) File name: 46821015001 Sequence Listing.txt; created Jul. 23, 2021, 37 KB in size.

BACKGROUND

Methods to quantify the constituents of gases have important applications in industry, agriculture, environmental monitoring, and healthcare. Ammonia is often a key gaseous component. For example, ammonia is commonly used to produce fertilizers and pharmaceuticals, and can be toxic if inhaled. In poultry farming, the ammonia levels need to be closely monitored and controlled as high levels lead to production losses, higher feed conversion ratios, compromised bird health, and non-compliance with new welfare guidelines. Environmental monitoring of ammonia is important because its toxicity has damaging effects on the ecosystem and human health. Accurate environmental monitoring of ammonia gas concentrations near cities requires sensitivity in the 20-30 ppb range. For potential biomedical applications, high levels of ammonia in the breath may indicate asthma and bacterial infections in the lungs, as well as chronic kidney disease (CKD). Healthy ammonia breath concentrations are usually sub-ppm (<1 ppm), ranging from ~30 ppb to 1800 ppb, and are typically elevated to multiple ppm (~1-15 or a mean ~5 ppm) in the case of renal damage and CKD. In children, breath ammonia levels increase even in the earliest stages of CKD. Renal and liver diseases can be tracked with ammonia breath levels, which are also useful for monitoring halitosis and epileptic patients.

Humidity sensors can play important roles in wearable devices for monitoring body position, respiration, hydration, and wound healing. Skin hydration levels can be indicative of various health and disease states.

Electronic biosensors are advantageous due to their compact size and easy integration, enabling portable point-of-care diagnostics. Various electronic sensors based on carbon nanotubes, silicon nanowires, metal oxides, and other hybrid materials have been developed for ammonia and humidity detection, but the majority lack the sensitivity, wearability, or both, as may be required for various environmental and health monitoring purposes.

SUMMARY

Gas sensors comprising protein nanowires are provided. The gas sensors can detect ammonia at low concentrations with high selectivity among various gases commonly found in breath, indicating the potential for disease monitoring in biomedical applications. The gas sensors can also be configured to detect changes in humidity, which can be an important metric related to diverse environments, human activities, and health.

An example of a gas sensor includes a biomaterial comprising electrically-conductive protein nanowires and at least two electrodes. The at least two electrodes are in operative arrangement with the protein nanowires and configured to provide a signal indicative of a change in conductivity of the protein nanowires. The conductivity of the protein nanowires is responsive to a change in concentration of a gas exposed to the biomaterial.

The conductivity of the protein nanowires can vary in response to, for example, changes in ammonia concentration (e.g., changes in ammonia concentration within a range of about 5 ppb to about 15,000 ppb) or changes in humidity or relative humidity (e.g., relative changes in humidity of between about 5% to about 100%).

The gas sensor can be self-powering. In particular, the protein nanowires can be configured to yield an electrical output (e.g., voltage, current), without an applied voltage, in response to exposure to moisture. The gas sensor can further comprise an energy store. Upon exposure to moisture, the energy store can be charged by an output voltage generated by the protein nanowires.

The at least two electrodes can be configured to apply a voltage to the biomaterial, for example, a voltage of about 0.1 V to about 5 V.

The protein nanowires can comprise a pilus structure (e.g., a type IV pilus structure), a cytochrome filament structure, or a combination thereof. For example, the protein nanowires can be of the bacterium G. sulfurreducens, including wild-type protein nanowires or modified protein nanowires. Alternatively, the protein nanowires can be synthetically assembled. The protein nanowires can comprise a structure assembled from protein monomers having an amino acid sequence as disclosed in Tables 1 and 2 herein.

The biomaterial can be included in the sensor as a film, for example a flexible film. The film can have a thickness of about 2 nm to about 500 nm, or of about 2 nm to about 100 nm. The film and electrodes can be disposed on a substrate, such as a substrate that provides for electrical and/or thermal insulation. The substrate can be a flexible substrate.

The at least two electrodes in operative arrangement with the biomaterial can be disposed in any configuration relative to the biomaterial to apply a voltage therethrough. The electrodes can be, for example, interdigitated electrodes. The electrodes can comprise a metal, such as Gold (Au), Silver (Ag), Copper (Cu), Nickle (Ni), Chromium (Cr), Titanium (Ti), Tantalum (Ta), Aluminum (Al), Tungsten (W), Carbon (C), Platinum (Pt), Palladium (Pd) or any combination thereof. For example, the electrodes can comprise a metal alloy.

The biomaterial can comprise a composite of protein nanowires and at least one other material, such as a material that modifies a conductive property of the protein nanowires, confers structural support to the protein nanowires, or a combination thereof. The material can be organic or inorganic.

The gas sensors can also be configured to be worn (e.g., on a person). An example of a wearable sensor includes a gas sensor and an attachment mechanism. For example, the attachment mechanism can be a flexible, adhesive substrate on which the biomaterial and the electrodes are disposed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 14A is a graph of current responses from an example protein-nanowire device placed close to the nose, measured at (red, top line) normal state and (gray, bottom line) after exercise.

FIG. 14B is a graph of current responses from an example protein-nanowire device placed on the hand palm (gray curve, left) and on the back of the hand (red line, right).

FIG. 14C is a graph of current responses from an example protein-nanowire device placed on the arm (gray, left) before and (red, right) after exercise.

FIG. 14D is a graph of current responses from an example protein-nanowire device to a finger's movements of (top) swiping across and (bottom) gradual elevating. The insets show the schematics of finger track, with the numbers indicating the positions.

FIG. 14E is a graph of a current response in an example protein-nanowire device with respect to the distance (D) to a vertical fingertip.

FIG. 14F is a re-constructed contour map of current signal with respect to a non-contact fingertip placed above a proof-of-concept 4×4 nanowire device matrix fabricated on a Si substrate (lower left inset), as illustrated in a schematic (upper left inset) of a non-contact objective using nanowire sensor arrays. The moisture adsorption in each sensor unit is relevant to the distance to the objective, which is further converted to current signal.

FIG. 19A is a cross-section SEM image of an example assembled protein nanowire film on a Si substrate (with 600 nm $SiO_2$). The image showed a dense film without visible holes. Scale bar, 1 μm.

FIG. 19B is a TEM image of a thin layer (e.g., <10 nm) of protein nanowires, showing that the nanowires were densely packed. In particular, in the aligned bundling region, the inter-wire spacing was inferred to be smaller than the wire diameter (e.g., 2-3 nm) and hence at sub-nanometer scale. Scale bar, 100 nm.

FIG. 20 is a graph of electric power generation (voltage) of an example protein nanowire device. Instant humidity gradient in percolative conductive films was shown to yield electric potential gradient and hence a measured voltage output.[8] Here we demonstrated that the protein-nanowire device could generate a ~0.13 V output voltage by a humidity gradient induced by a breath, which could be used to charge up a capacitor (10 μF). Note that because the protein nanowire device had a substantially increased resistance at lower RH (FIG. 13A), the discharging time (RH reduced after breath) was much slower than the charging time using the circuit shown in the inset.

DETAILED DESCRIPTION

A description of example embodiments follows.

Figure 1A:
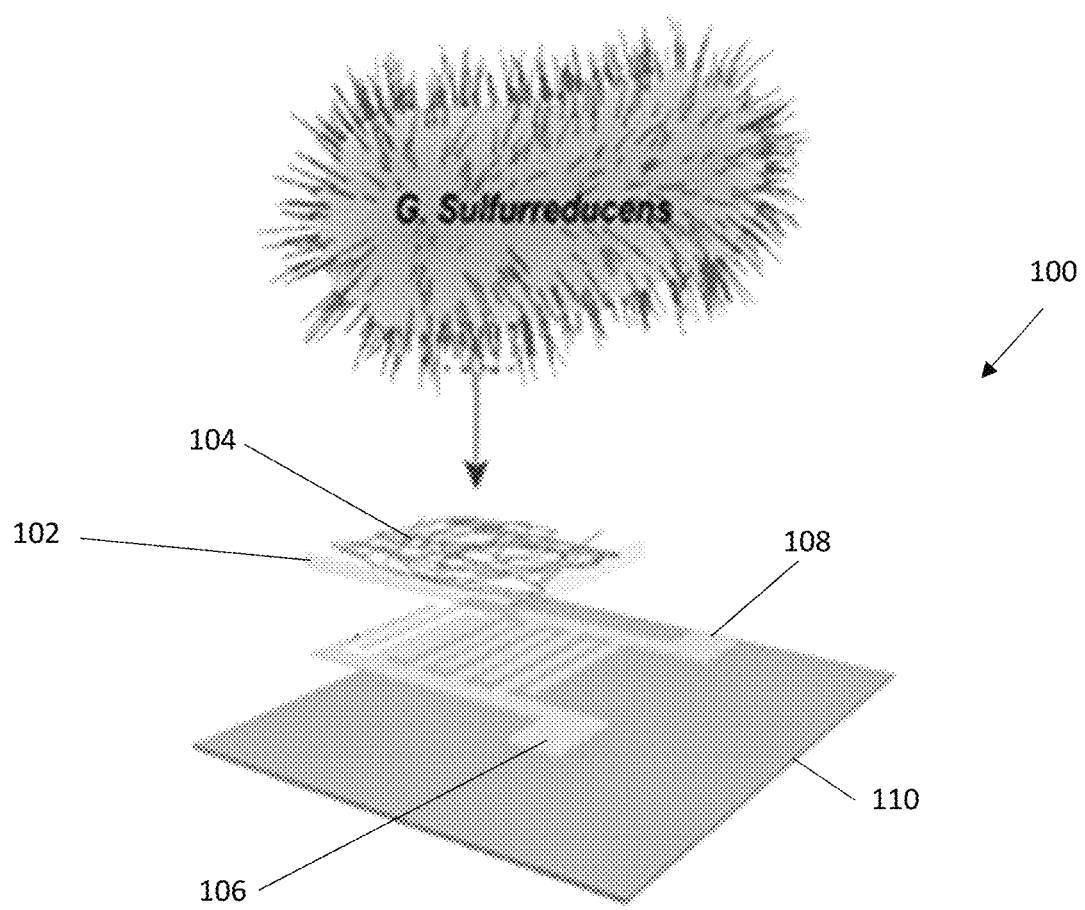
FIG. 1A is an exploded view of an example of a gas sensor.
Figure 1B:
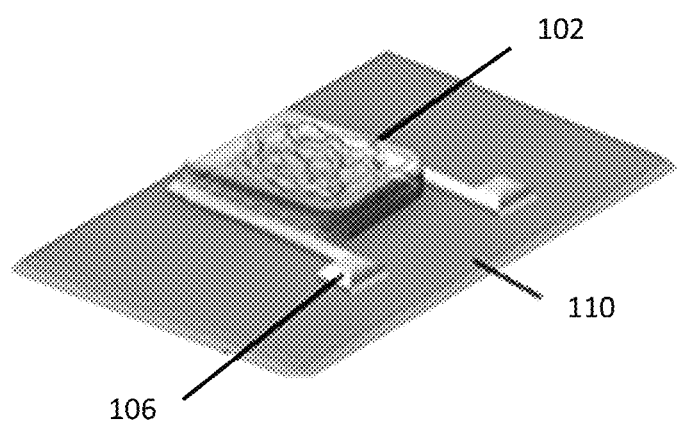
FIG. 1B is a perspective view of the gas sensor of FIG. 1A in an assembled state.

An example of a gas sensor is shown in FIGS. 1A-1B. As illustrated, the sensor 100 includes a biomaterial 102 comprising electrically-conductive protein nanowires 104, for example, as harvested from the bacterium *G. sulfurreducens*. The biomaterial 102 can be a film, as illustrated, which includes or is disposed over the electrodes 106, 108. The electrodes 106, 108 are in operative arrangement with the protein nanowires to provide a signal indicative of a change in conductivity of the protein nanowires in response to a change in a concentration of a gas exposed to the biomaterial 102. As illustrated, the electrodes 106, 108 are interdigitated electrodes. The electrodes can be in any pattern or configuration (e.g., interdigitated, spirally interdigitated, concentrically patterned, radially patterned, cascade patterned, etc.). As illustrated, the electrodes 106, 108 are disposed between the biomaterial film 102 and a substrate 110. The electrodes can alternatively be disposed at opposing surfaces of the film.

The electrodes 106, 108 and film 102 can be disposed on a substrate 110. The substrate can be electrically insulating, thermally insulating, or both. The substrate can also provide for attachment of the sensor to another device or to a subject. For example, the substrate 110 can be a flexible, adhesive substrate configured to be attached to skin. Alternatively, the substrate can be a rigid substrate. Non-limiting examples of substrates include polyimide (PI) substrates, polydimethylsiloxane (PDMS) substrates, and polyethylene terephthalate (PET) substrates.

As used herein, the term "biomaterial" is a material that is derived from or mimics a material produced by a biological organism. For example, a biomaterial can include biological macromolecules, such as proteins, nucleic acids, carbohydrates, or any combination thereof. The biomaterial can be provided in a variety of structural forms, such as a biofilm, a biopolymer or a matrix of crosslinked proteins. For example, the biomaterial can comprise protein polymers having dimensions suitable for forming protein nanowires, as described further herein. The nanowires can be cross-linked to one another to form a matrix, or dispersed in an organic or inorganic medium to form a composite.

The biomaterial can be obtained (e.g., isolated, purified, extracted, secreted, harvested) from a biological source, such as a bacterium. Alternatively, the biomaterial can be produced synthetically or recombinantly using standard methods, techniques and reagents.

In one example, a sensor includes a biomaterial comprising nanowires formed of proteins (e.g., pilin monomers, cytochromes). The protein nanowires can comprise a pilus structure, a cytochrome filament structure, or a combination thereof. For example, the pilus structure can be a type IV pilus structure, such as that generated by the bacterium *G. sulfurreducens*. The cytochrome filament structure can be, for example, an OmcS filament structure, such as that generated by the bacterium *G. sulfurreducens*.

The nanowires can be wild-type protein nanowires generated by a bacterium, such as *G. sulfurreducens*. Alternatively, the nanowires can be wild-type protein nanowires generated by other microbes. Tables 1 and 2 below include examples of amino acid sequences of protein monomers that can be arranged into a structure, such as a nanowire, for inclusion in a sensor.

TABLE 1

Non-limiting Examples of Protein Monomer Sequences Capable of Forming Protein Nanowires when Polymerized

| | |
|---|---|
| SEQ ID NO: 1 | FTLIELLIVVAIIGILAAIAIPQFSAYRVKAYNSAASSDLRNLKTALESAFADD QTYPPES |
| SEQ ID NO: 2 | FTLIELLIVVAIIGILAAIAIPQFAAYRQKAFNSAAESDLKNTKTNLESYYSEH QFYPN |
| SEQ ID NO: 3 | FTLIELLVVVAIIAILAAIAIPQFAKYRENAAKASAVADAKNIATAIESYYAD TQSFPSSISDGSIVPLGTQTFSLSKNNSFKGYYYNNPSYTFVVSNTAFNRSVT FNSATGGVDVNVW |
| SEQ ID NO: 4 | FTLVELMIVVAIIGILAAVAIPQFAQYRIRGFNSSALSDVRNLTTAQEAFFAD WLRYAVTHEAADVTEVKATGDLLEGPSTGAMVLAQWARQAHQQLPLAIG NGVVMQADVIPATAVSYVAISKHLQGNTMYGATNTSTAIHRDQETLVPGQ GGDVLPITGYMPEPHETDDPFIDHEEFEAQ |
| SEQ ID NO: 5 | FTLIELLVVVAIIGILAAIAIPQFAKYRINAFNSAAQSDLANVKSALESYYAE NFTYPSP |
| SEQ ID NO: 6 | FTLIELMIVIAIIGILAAIAIPQFQQYRTRGYNTAAKADAKNAYTAAQAYFSD HPSVTISSITDLANYGFKASADVTTTAAGDMDGLAITAKHSASDTTYQVDS QGTITP |
| SEQ ID NO: 7 | FTLIELMIVIAIIGILAAIAIPQFTQYRKRAYDASSKADLKSAYTAAQAWFND NPSGTLPAATITSATTTGELPGNGFKASTGVTATVTSGTMGTFSIATTHSQG TKTYNITAGGTLTES |
| SEQ ID NO: 8 | FTLIELMIVVAIIGILAAIAIPQFANYRTKGYNTKAKAELKSAYTACQAYFSD NPGATACANATLGGFNNSSDVNIAVGLSTPTGWTATASHIGGNQTFTVDN GGRITP |
| SEQ ID NO: 9 | FTLVELMIVVAIIGILAAVAVPYYQKYIQKSRMVSKVFPGMHAIETNMGTY FSFKNTLLDVGSTATFGQFVQDADTKCFSPSWAGEYLLITIKDPTLCQELKA LTGMTLSATPRMDTSRTKIRGWALAGPLAVQLGLEGEQ |
| SEQ ID NO: 10 | FTLIELMIVVAIIAILAAIAIPQYKKFQLKAKTSEAKANLGSIRSCEEAYSAET DNYVFCGWTPSNAPTAAGQAWVTTSGHEGFVSIGFAPAGTSRYCYCVGGS VNTAGTDAATNAFNEGNVDIYMTAKGDLDGDGSNQWFYATDEDLKVMA DYSQDDF |
| SEQ ID NO: 11 | FTLVELMIVVAIIGILAAVAVPYYQKYIQKARLTSKVIPGIHSIQTDLATYFSF QQMFPGAGATVNAMFTDANTHCFTPTVTSAAGATSNFKITFAIVGAGCTEL SSLYNQTITASPILGNNAQVITGWTFGGTLAANMGLAGAQ |
| SEQ ID NO: 12 | FTLIELLIVIAIIGVLAAIAIPAYTGYTKKAKVGEIIHALGAIKSAVSVYYSEA GATTDATTADLIRTTYGVDVPTGRASFQYTATSREIQATSKITGVTGTMTLT GSTDFKTWTWDGTMDKAYIPKN |
| SEQ ID NO: 13 | FTLIELMIVIAIIGILAAIAIPNFVSYRKKAYNRTAQADLSSAYSTVMAYYAD EKHKEIDNFTLDNLKDAGFKQTVGVAVTVTSVNFQDFELTARHSQGDIVY TIDAAGARSHN |
| SEQ ID NO: 14 | FTLIEILVALFLAILVASSLVTVFQMSHHIFYRDFSRSELQYMARKAMEDIID YVVQAQPDSLAVNGAEGSQLEFILSSGAKIQYSQGANYWLYRKGPDSGPP QPIVEQIAKVKFCLSGPHILTVDVVAGNEKNSFTLTQMIVPRAEIDENDWLN SL |
| SEQ ID NO: 15 | FTLVELMVVLLIIGILVAIAIPIYNKTQENAQKRACQSNLRTLDSAAAQYGA ATGNYPTDPLNNANFVGENGYVKTKPTCPAGGVYNYDATNGKFSCNVPD HVYP |
| SEQ ID NO: 16 | FTLIELILALGLLSLIMTTSFTIYSAGQKTYEYENSKIFVQQNARQAFLWLST SIKQARSVEVMSENSIKTVAGDGETIIYYFKNGVLYREKNNGINPIAELSQL KFKQPKDKQYIEIFLAAQGKEGDDIIIKTKATPFGLWVN |
| SEQ ID NO: 17 | FTMIEMMVVLIIIAVLIAGGIRFYLGYVERAKVTKAKSEITTMQAALDSYYA EKGEYPDDENDRELVKAGLATDRISISTEGNDSIQYIYEGGGNSYKIITTATF RAGKLVGEGQDGKSTEPDFGSGE |

TABLE 2

Non-limiting Examples of Type IV Pilin Monomer Sequences

*Geobacter metallireducens*

SEQ ID NO: 18  FTLIELLIVVAIIGILAAIAIPQFAAYRQKAFNSAAESDLKNTKTNLESYYSEH
QFYPN

*Calditerrivibrio nitroreducens*

SEQ ID NO: 19  FTLIELLVVVAIIAILAAIAIPQFAKYRENAAKASAVADAKNIATAIESYYAD
TQSFPSSISDGSIVPLGTQTFSLSKNNSFKGYYYNNPSYTFVVSNTAFNRSVT
FNSATGGVDVNVW

*Desulfurvibrio alkaliphilus*

SEQ ID NO: 20  FTLVELMIVVAIIGILAAVAIPQFAQYRIRGFNSSALSDVRNLTTAQEAFFAD
WLRYAVTHEAADVTEVKATGDLLEGPSTGAMVLAQWARQAHQQLPLAIG
NGVVMQADVIPATAVSYVAISKHLQGNTMYGATNTSTAIHRDQETLVPGQ
GGDVLPITGYMPEPHETDDPFIDHEEFEAQ

*Felxistipes sinusarabici*

SEQ ID NO: 21  FTLIELLVVVAIIGILAAIAIPQFAKYRINAFNSAAQSDLANVKSALESYYAE
NFTYPSP

*Synthrophus aciditrophicus*

SEQ ID NO: 22  FTLIELMIVIAIIGILAAIAIPQFQQYRTRGYNTAAKADAKNAYTAAQAYFSD
HPSVTISSITDLANYGFKASADVTTTAAGDMDGLAITAKHSASDTTYQVDS
QGTITP

Syntrophus gentianae

SEQ ID NO: 23  FTLIELMIVIAIIGILAAIAIPQFTQYRKRAYDASSKADLKSAYTAAQAWFND
NPSGTLPAATITSATTTGELPGNGFKASTGVTATVTSGTMGTFSIATTHSQG
TKTYNITAGGTLTES

Smithella sp. F21

SEQ ID NO: 24  FTLIELMIVVAIIGILAAIAIPQFANYRTKGYNTKAKAELKSAYTACQAYFSD
NPGATACANATLGGFNNSSDVNIAVGLSTPTGWTATASHIGGNQTFTVDN
GGRITP

Syntrophobacter fumaroxidans

SEQ ID NO: 25  FTLVELMIVVAIIGILAAVAVPYYQKYIQKSRMVSKVFPGMHAIETNMGTY
FSFKNTLLDVGSTATFGQFVQDADTKCFSPSWAGEYLLITIKDPTLCQELKA
LTGMTLSATPRMDTSRTKIRGWALAGPLAVQLGLEGEQ

Syntrophobacter sp. DG_60

SEQ ID NO: 26  FTLIELMIVVAIIAILAAIAIPQYKKFQLKAKTSEAKANLGSIRSCEEAYSAET
DNYVFCGWTPSNAPTAAGQAWVTTSGHEGFVSIGFAPAGTSRYCYCVGGS
VNTAGTDAATNAFNEGNVDIYMTAKGDLDGDGSNQWFYATDEDLKVMA
DYSQDDF

Syntrophobacter sp. SbD1

SEQ ID NO: 27  FTLVELMIVVAIIGILAAVAVPYYQKYIQKARLTSKVIPGIHSIQTDLATYFSF
QQMFPGAGATVNAMFTDANTHCFTPTVTSAAGATSNFKITFAIVGAGCTEL
SSLYNQTITASPILGNNAQVITGWTFGGTLAANIVIGLAGAQ

Syntrophorhabdus aromaticivorans

SEQ ID NO: 28  FTLIELLIVIAIIGVLAAIAIPAYTGYTKKAKVGEIIHALGAIKSAVSVYYSEA
GATTDATTADLIRTTYGVDVPTGRASFQYTATSREIQATSKITGVTGTMTLT
GSTDFKTWTWDGTMDKAYIPKN

*Desulfatibacillum alkenivorans* PilA

SEQ ID NO: 29  FTLIELMIVIAIIGILAAIAIPNFVSYRKKAYNRTAQADLSSAYSTVMAYYAD
EKHKEIDNF TLDNLKDAGFKQTVGVAVTVTSVNFQDFELTARHSQGDIVY
TIDAAGARSHN

*Syntrophomonas zehnderi* PilA

SEQ ID NO: 30  FTLIEILVALFLAILVASSLVTVFQMSHHIFYRDFSRSELQYMARKAMEDIID
YVVQAQPDSLAVNGAEGSQLEFILSSGAKIQYSQGANYWLYRKGPDSGPP
QPIVEQIAKVKFCLSGPHILTVVAGNEKNSFTLTQMIVPRAEIDENDWLN
SL

TABLE 2-continued

Non-limiting Examples of Type IV Pilin Monomer Sequences

*Syntrophaceticus schinkii* PilA

SEQ ID NO: 31  FTLVELMVVLLIIGILVAIAIPIYNKTQENAQKRACQSNLRTLDSAAAQYGA
ATGNYPTDPLNNANFVGENGYVKTKPTCPAGGVYNYDATNGKFSCNVPD
HVYP

*Tepidanaerobacter acetatoxydans* PilA

SEQ ID NO: 32  FTLIELILALGLLSLIIVITTSFTIYSAGQKTYEYENSKIFVQQNARQAFLWLST
SIKQARSVEVMSENSIKTVAGDGETIIYYFKNGVLYREKNNGINPIAELSQL
KFKQPKDKQYIEIFLAAQGKEGDDIIIKTKATPFGLWVN

*Thermacetogenium phaeum* PilA

SEQ ID NO: 33  FTMIEMMVVLIIIAVLIAGGIRFYLGYVERAKVTKAKSETTTMQAALDSYYA
EKGEYPDDENDRELVKAGLATDRISISTEGNDSIQYIYEGGGNSYKIITTATF
RAGKLVGEGQDGKSTEPDFGSGE

The nanowires can also be edited protein nanowires, for example, nanowires derived from or mimicking naturally-occurring protein nanowires, which have been modified. For example, one or more amino acid groups can be deleted, inserted, or substituted with another amino acid group. Examples of modified nanowires, and methods of producing same, are described in United States Patent Application Publication No. US 2018/0371029 A1, the contents of which are incorporated herein by reference in their entirety. The nanowires may be functionalized to include surface exposed peptides (e.g., ligands). Examples of functionalized nanowires that include surface-exposed ligands, and methods of producing same, are described in Ueki T., et al., Decorating the Outer Surface of Microbially Produced Protein Nanowires with Peptides, *ACS Synth Biol.* 2019 Aug. 16; 8(8): 1809-1817, the contents of which are incorporated herein by reference in their entirety.

The nanowires can be synthetically generated, for example by peptide self-assembly or by expression from a modified bacterium, such as *E. coli*. Example methods of producing protein nanowires in a modified bacterium are described in Ueki T., et al., An *Escherichia coli* Chassis for Production of Electrically Conductive Protein Nanowires, *ACS Synth Biol.* 2020 Mar. 20; 9(3):647-654, the contents of which are incorporated herein by reference in their entirety.

The nanowires can be produced by recombinant methods. Example methods of producing protein nanowires by recombinant methods are described in International Application No. PCT/US2020/061609, filed on Nov. 20, 2020, and in Ueki T., et al., An *Escherichia coli* Chassis for Production of Electrically Conductive Protein Nanowires, *ACS Synth Biol.* 2020 Mar. 20; 9(3):647-654, the contents of which are incorporated herein by reference in their entirety.

The nanowires can be electrically conductive. Various types of pili and filaments, such as archaella, have been found to be conductive and can be suitable for inclusion in the biomaterial of a sensor. One example of electrically-conductive nanowires are the pili structures expressed by the bacterium *G. sulfurreducens*.

Figure 2:
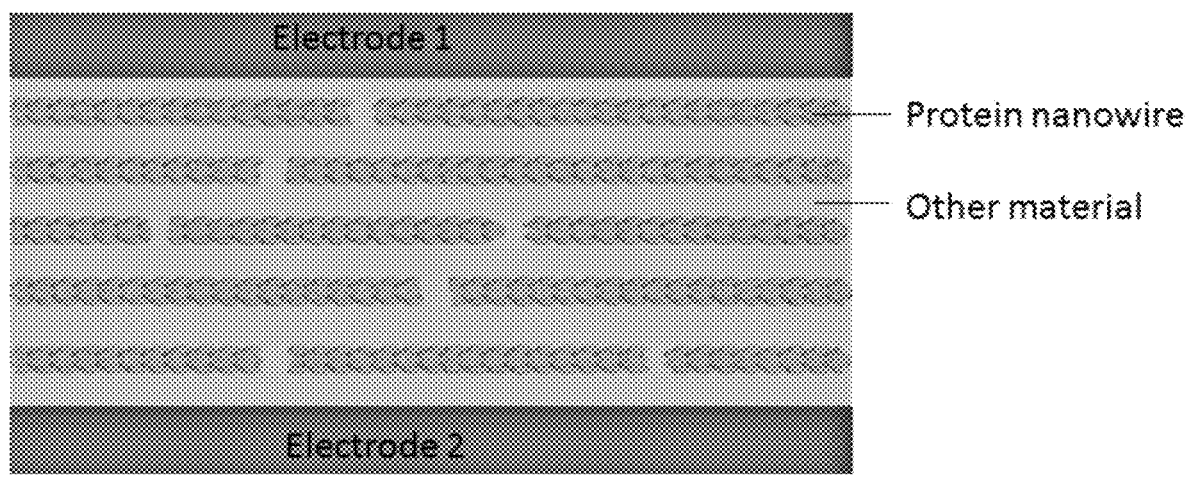
FIG. 2 is a schematic of a gas sensor including a composite biomaterial.

The biomaterial can include a composite of protein nanowires and at least one other material. For example, the other material can be one that modifies a conductive property of the protein nanowires, confers structural support to the protein nanowires, or a combination thereof. An example of a composite biomaterial arranged with two electrodes of a sensor is shown in FIG. 2. The composite biomaterial can include any combination of inorganic and organic elements, as well as other biomaterials. Examples of composite materials fabricated with protein nanowires are described in U.S. Patent Pub. No. 2020/0090830, the entire contents of which are incorporated herein.

The other material forming the composite can be inorganic. For example, the other material can be a conventional dielectric material (e.g., Si, SiOx, SiNx, HfO2, Al2O3, etc.), a two-dimensional material (e.g., graphene, graphene oxides, transition metal dichalcogenides (e.g., MoS2), boron nitride, etc.), or any combination thereof.

The other material forming the composite can be a biomaterial. For example, the other material can be a polysaccharide (e.g., chitosan, carrageenan, starch, etc.), a protein structure (e.g., silk, sericin, ferritin, gelatin, etc.), a nucleic acid structure (e.g., DNA, RNA), or any combination thereof.

The other material forming the composite can be organic. For example, the other material can be a polymer (e.g., polyvinyl alcohol, polyvinylpyrrolidone, poly(4-vinylphenol), parylene, PEDOT:PSS, etc.) or combination of polymers.

The biomaterial can be provided in the device as a film. For example, a monolayer of protein nanowires can be provided, which can provide for a film thickness of about 2 nm. The protein nanowires can be provided in a film having a thickness and/or length of about 2 nm to about 500 nm (e.g., 1.5 nm, 2 nm, 5 nm, 10 nm, 50 nm, 100 nm, 200 nm, 300 nm, 400 nm, 500 nm, and 510 nm), or of about 2 nm to about 100 nm. Example preparations of protein nanowires are provided in the appended manuscript.

A gas sensor can be self-powering, as shown in FIG. 20. For example, the gas sensor can include an energy store (e.g., a capacitor) such that, upon exposure to moisture, an output voltage generated by the biomaterial provides for charging of the energy store. Examples of power generation by protein nanowires are further described in Liu X., et al., Power Generation from Ambient Humidity Using Protein Nanowires, *Nature* 2020 Feb. 17; 578: 550-554, and in International Pub. No. WO2020/069523, the entire contents of which are incorporated herein by reference.

Electronic sensors based on biomaterials can provide for green technologies that are low cost, renewable, and eco-friendly. As described in the examples that follow, it has been demonstrated that gas sensors made from protein nanowires harvested from the microorganism *Geobacter*

*sulfurreducens* can provide for detection and/or measurement of various analytes, including ammonia and humidity. Example nanowire sensors were shown to respond to a broad range of ammonia concentrations (10 to $10^6$ ppb), which encompasses a range relevant to various industrial, environmental, agriculture, and biomedical applications. Example sensors also demonstrated high selectivity to ammonia compared to moisture and other common gases found in human breath. Example protein nanowire sensors were also developed for humidity sensing, an important metric related to diverse environments, human activities, and health. For example, humidity sensors play important roles in wearable devices for monitoring body position, respiration, hydration, and wound healing.

Sustainably produced biomaterials can also greatly improve biocompatibility of wearable sensor technologies while reducing the energy and environmental impacts of materials fabrication and disposal. Example sensors were fabricated in which the sensing element was a thin (ca. 2 μm) film of electrically conductive protein nanowires harvested from the microbe *Geobacter sulfurreducens*. The sensor rapidly responded to changes in humidity with high selectivity and sensitivity. The sensor was integrated on a flexible substrate as a wearable device, enabling real-time monitoring of physiological conditions such as respiration and skin hydration. Non-contact body tracking was demonstrated with an array of example sensors that detected a humidity gradient at distance from the skin with high sensitivity. Humidity gradients induced directional charge transport in the protein nanowires films, enabling the production of a current signal without applying an external voltage bias or powerless sensing.

Various electronic sensors based on carbon nanotubes, silicon nanowires, metal oxides, and other hybrid materials have been developed for ammonia detection, but the majority lack the sub-ppm sensitivity required for environmental and health monitoring. Incorporating low-dimensional nanomaterials for improved surface coupling and signal transduction has, in some instances, enabled ammonia detection at tens of ppb based on conductance modulation through field or charge effects introduced by ammonia adsorption. However, the selectivity of these sensors for ammonia and their susceptibility to nonspecific interference is not well known, as surface adsorbates can have generic charge or field effects that modulate the conductance in nanomaterials. Ammonia sensors based on optical waveguide techniques typically incorporate pH sensing dyes that are responsive to adsorbed ammonia. Optical waveguide sensors can achieve high sensitivity for ammonia detection, but are often too large, complex, and expensive for portable applications.

Electronic sensors are advantageous for wearable applications ranging from energy harvesting, motion control, physiological monitoring, disease diagnostics, to biomedical remedies. Sustainably produced, biocompatible and flexible electrically conductive materials are needed for the development of next-generation wearable sensors. Biologically produced materials are especially attractive because they share many properties with biological tissues. For example, silk has been incorporated into various sensing devices. However, silk lacks native conductivity to be the active conductive element in a conventional sensor structure.

Electrically conductive protein nanowires (e-PNs) can provide for an alternative sensing component of electronic sensors. In addition, protein nanowires can be microbially produced from renewable feedstocks at a fraction of the energy requirements for fabricating silicon nanowires or carbon nanotubes, without harsh chemical processes or toxic components in the final product. Although they are physically and chemically robust (functional at pH 2-10.5 and temperatures up to ca. 100° C.), protein nanowires are biodegradable, eliminating the growing environmental and health concerns associated with electronic waste.

Electrically conductive protein nanowires (e-PNs) harvested from the microbe *Geobacter sulfurreducens* are intrinsically conductive. Conductivity of ePNs can be tuned with genetic modifications to yield a range of conductivities (ca. 10 μS/cm-1 kS/cm) in thin (≤3 nm) wires. See D. R. Lovley, *Curr. Opin. Electrochem.* 2017, 4, 190 and D. R. Lovely, D. Walker, *Front. Microbiol.* 2019, 10, 2078, the entire contents of which are incorporated herein by reference. The conductivity of ePNs is highly responsive to pH, with changes of 5000-fold in individual conductivity over a range of pH 2-10.5. See R. Y. Adhikari, et al. *RSC Adv.* 2016, 6, 8354, the entire contents of which are incorporated herein by reference. These results demonstrate that e-PN conductivity is highly sensitive to changes in surface charge state, a desirable feature for designing sensing capabilities because surface adsorbates often induce a change in surface charge. Although they are comprised of protein, *G. sulfurreducens* e-PNs are highly robust with stability over a broad pH range (e.g., pH 2-10), at high temperatures (>100° C.) and in organic solvents. Unlike silicon nanowires, e-PNs do not dissolve in physiological fluids. e-PNs can be mass-produced from inexpensive renewable feedstocks without the need for hazardous chemicals in processing and there are no toxic components in the final product. They are fabricated from renewable feedstocks, with energy requirements 100-fold less than for processing silicon. Thus, e-PNs are a 'green' electronic material, with low-cost, low-energy, and low-waste properties that are desirable for dispensable wearable devices.

EXEMPLIFICATION

Example 1. Fabrication of Protein-Nanowire Sensors for Ammonia Detection

Protein nanowires (FIG. 3) were purified from cultures of *Geobacter sulfurreducens* and suspended in water. The protein nanowires were purified as generally described in Tan, Y. et al. Expressing the *Geobacter metallireducens* PilA in *Geobacter sulfurreducens* Yields Pili with Exceptional Conductivity. *MBio.* 2017, 8, 02203-16, the entire contents of which are incorporated herein by reference.

Figure 3:
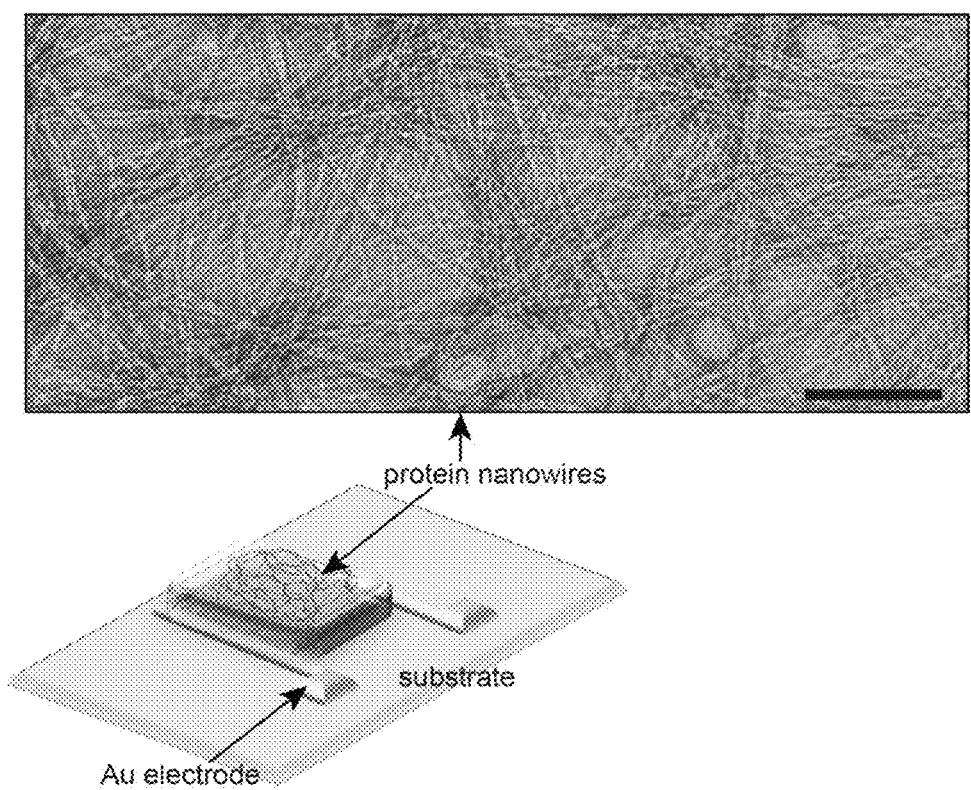
FIG. 3 is a schematic of an example fabricated sensor device made by drop-casting protein nanowires on gold electrodes and a transmission electron microscopy (TEM) image of harvested protein nanowires for the example sensor device. Scale bar, 100 nm.

Interdigitated electrodes were fabricated on polyethylene terephthalate (PET) substrates with standard lithography, metal deposition (Cr/Au, 3/50 nm), and lift-off processes. Scotch tape was used to define a 10×2 mm area to be deposited with the protein nanowire film. The prepared protein nanowire solution was drop-casted across the Au electrodes on the substrate, and the water in the protein nanowire solution was dried at 23° C., to fabricate the thin-film sensor structure (FIG. 3). Film thickness was roughly estimated using an optical profilometer.

Example 2. Electrical Measurement Setup for Ammonia Detection

Figure 7:
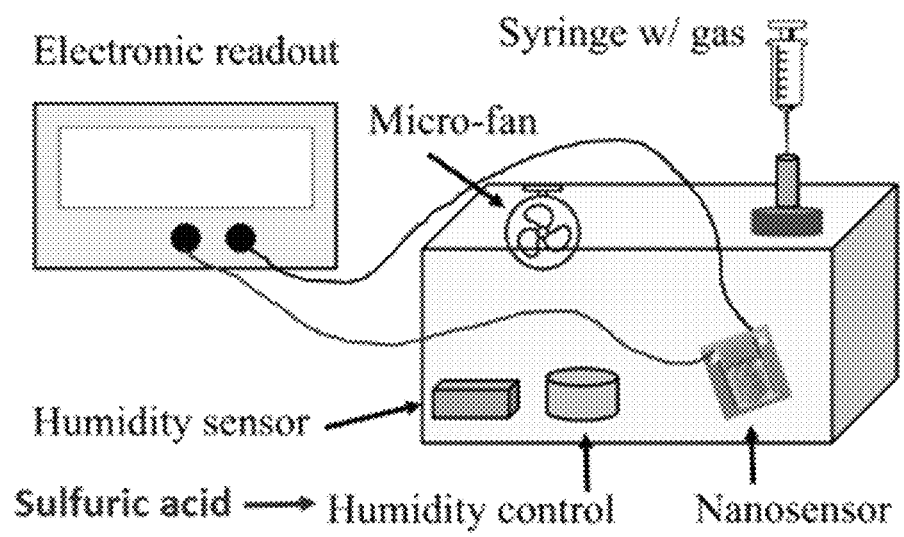
FIG. 7 is a schematic of a vapor chamber testing system and electronic readout.

The protein nanowire sensor was placed in a custom-built airtight vapor chamber to control gas concentration (FIG. 7). A gas injection port was designed to inject ammonia gas via syringe into the chamber. A miniature fan was installed within the vapor chamber to disperse the gas throughout the chamber. The baseline humidity in the chamber was controlled by tuning the equilibrium vapor pressure of sulfuric acid solutions by varying the concentration of sulfuric acid. The humidity was measured continuously using a hygrometer (Reed 6030). Temperature was kept constant at 23° C.

During electrical measurements, a constant voltage of 1 V was applied to the sensor and the current was measured continuously by a semiconductor parameter analyzer (Keithley 4200-SCS). The vapor chamber was sealed to maintain a constant relative humidity level. A syringe was used to extract volatilized gas from the head space of a container of ammonium hydroxide (32%, Merck) in-situ and inject the gas directly into the vapor chamber using the gas injection port. The concentration of the injected ammonia gas was calculated using the ideal gas law, given the known partial pressure of ammonia in the ammonium hydroxide solution. After the sensor response reached a steady state signal, ammonia gas was purged from the vapor chamber, returning the current output to its original state.

To test the pure humidity response of the sensor, the relative humidity was varied from 45-100% by evaporating a droplet of water inside the vapor chamber. The current output was continuously measured, as was the humidity level using the hygrometer. To analyze the isolated effect of water vapor (e.g., compared to a mixture of ammonia and water vapor), pure water vapor was injected via the syringe method.

To elucidate the response of protein-nanowire sensor to various gases, the syringe injection method was used to expose the sensor to gases and volatile organic compounds (VOCs) that are commonly found in the breath. Physiological concentrations of 1 ppm ammonia, acetone, and ethanol gases were tested by injecting gas extracted from the headspace of containers of liquid. Nitrogen and carbon dioxide were directly injected as pure gases.

Figures 4A, 4B, 4C:
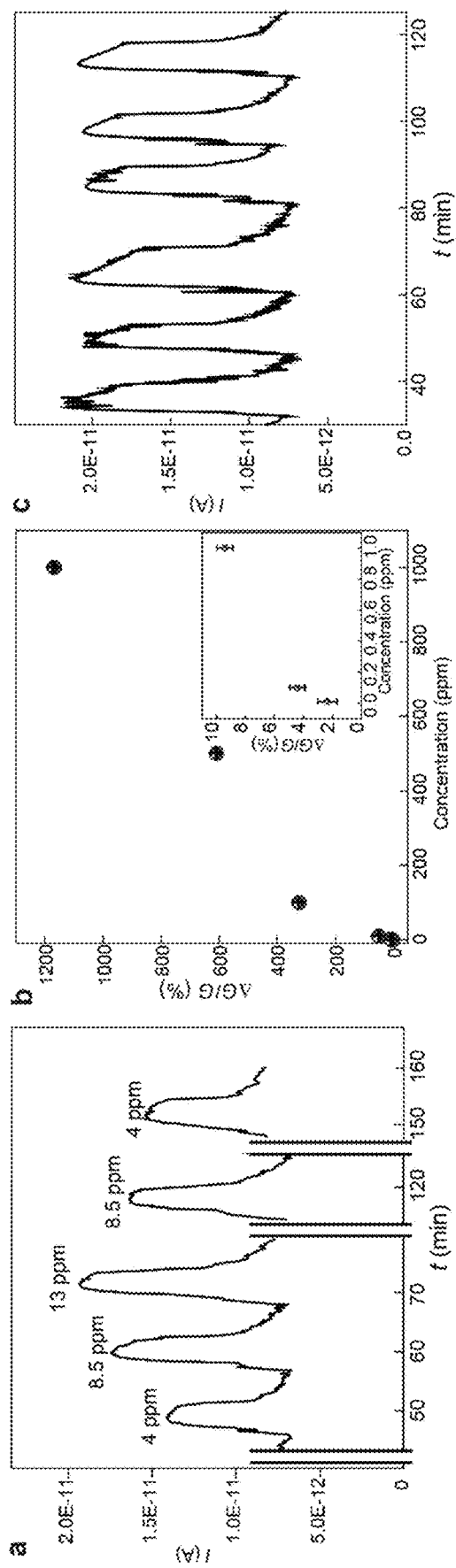
FIG. 4A is a graph of a real-time response of a prototype nanowire sensor to injected ammonia gas at a baseline relative humidity of 45%.
FIG. 4B is a graph of prototype sensor response (AG/G %) with respect to a wide range of ammonia concentrations (10 ppb to 1000 ppm) at 55% RH. The inset shows the zoom-in response from 10 ppb to 1 ppm.
FIG. 4C is a graph illustrating reproducible responses from the prototype sensor by repeated injection of 8.5 ppm ammonia at 50% RH. The temperature was kept constant at 23° C.
Figure 8:
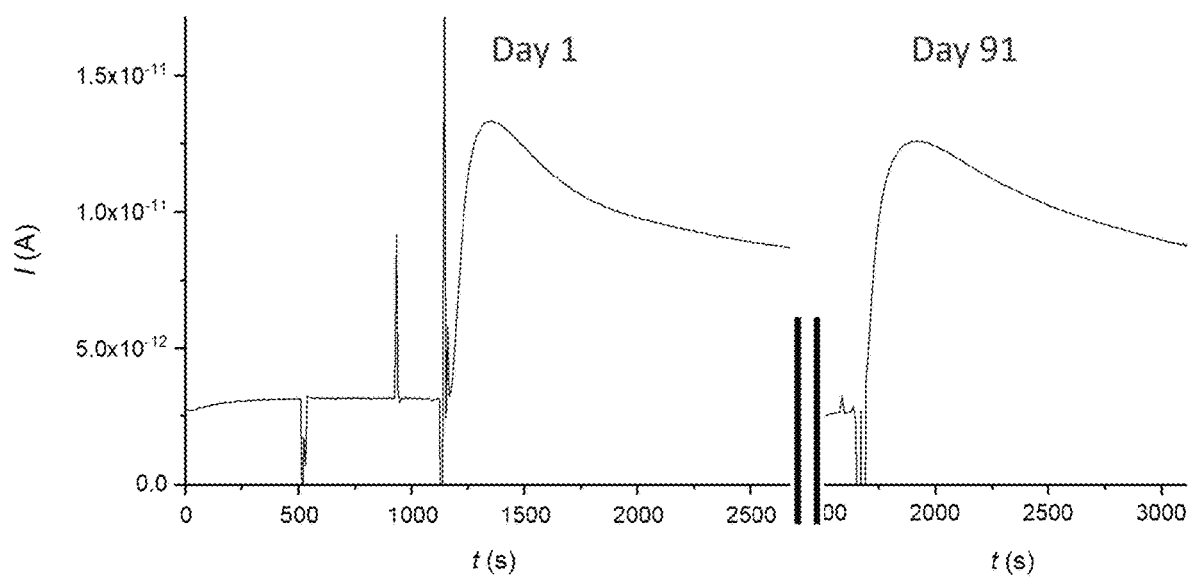
FIG. 8 is a graph illustrating a stable, repeatable, and consistent response of a prototype sensor to 100 ppm ammonia gas over 90 days at 47-57% RH. The initial sharp spikes were artifacts (e.g., mechanical perturbation) during gas injection.

Example 3. Results Obtained from Prototype Protein Nanowire Sensors for Ammonia Detection The sensors were made by depositing a protein-nanowire suspension on interdigitated electrodes to yield a thin conductive film after air-drying (FIGS. 1, 3). It was previously shown that a thicker protein nanowire film yielded a lower adsorption of gas molecules (e.g., moisture) due to an increasing diffusion barrier to deeper layers. This may result from a reduced effective surface-to-volume ratio in thicker films. A thin layer of protein nanowires (e.g., ~40 nm with $\sigma=2.3\times10^{-7}$ S/cm) was used for testing for potentially improved sensitivity. The nanowire sensor was biased at a constant DC voltage of 1 V, and current was monitored in real-time as dilute ammonia gas was repeatedly injected into and purged from the vapor testing chamber (FIG. 7). Increasing the concentration of ammonia gas introduced to the chamber yielded a distinct increase in current (FIG. 4A). The sensor responded to a broad range of ammonia concentrations (FIG. 4B), with a lower detection limit of 10 ppb. This is, to our knowledge, among the lowest detection limits of existing electronic ammonia sensors (Table 3). Sensor sensitivity, defined as the relative conductance change (AG/G) per ppm, increased at lower concentrations (FIG. 4B), which is commonly observed in other ammonia sensors. The dynamic response range of the sensor is suitable for most environmental and biomedical applications (e.g., 30-15,000 ppb). The response time of the sensor, defined as the time it takes for the baseline current signal to increase to 90% of its peak saturation value, was 46 seconds, which is faster than most existing electronic ammonia gas sensors that can achieve low (e.g., sub-ppm) detection (Table 3). Repeated exposures to 8.5 ppm ammonia gas demonstrated that the electrical response was consistent and reproducible (FIG. 4C). As protein nanowires are highly stable in ambient environments, the protein-nanowire sensors demonstrated robust functionality, maintaining a consistent response when tested repeatedly over 90 days (FIG. 8). The result is consistent with a previous study demonstrating long-term stability of a protein nanowire device in an ambient environment, which can be attributed to the material robustness in protein nanowires even in harsh environments.

TABLE 3

Comparison of protein nanowire sensor with representative electronic ammonia gas sensors.

| Material | Sensitivity range (ppb) | Measured limit of detection (ppb) | Response time (s) | Reference |
|---|---|---|---|---|
| Protein nanowires (this work) | 10-1,000,000 | 10 | 46 | This work |
| SWCNT/indium-tin oxide (ITO) nanoparticles | 20-3,400,000 | 20 | ~60; not reported | 4, 43 |
| SWCNT/COOH- functionalization | 30-30,000 | 30 | 60 | 25 |
| Si NW/SiO$_2$ | 170-20,000 | 170 | 900 | 29 |
| Si NW/Tellurium nanoparticles | 10,000-400,000 | 10,000 | 5 | 28 |
| MoO$_3$ | 50-1,000 | 50 | not reported | 44 |
| Perovskite halide (CH$_3$NH$_3$PbI$_3$) | 1,000-50,000 | 1,000 | ~100-130 | 41 |
| rGO/Co$_3$O$_4$ nanofibers | 5,000-100,000 | 5,000 | 4 | 40 |

Figure 9A:
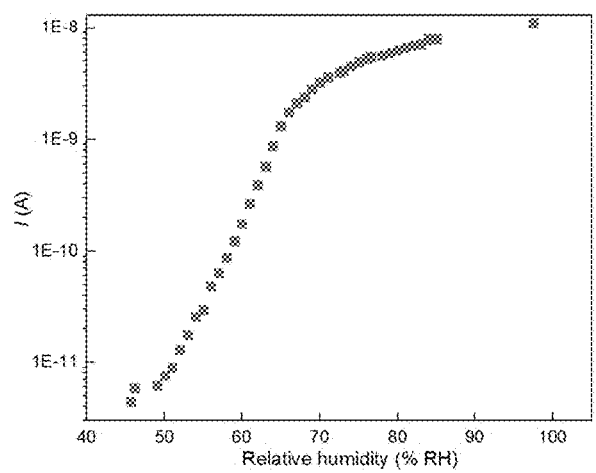
FIG. 9A is a graph of a current output of a protein-nanowire device measured as a function of relative humidity in the vapor chamber environment.
Figure 10A:
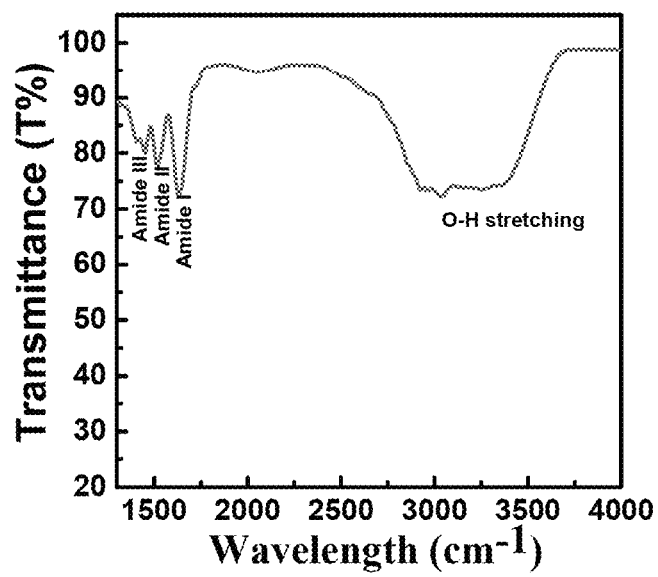
FIG. 10A is a Fourier-transform infrared spectroscopy (FTIR) spectrum of a prototype protein nanowire film (~200 nm thickness) at relative humidity (RH) of 40%. The broad peak ~3400 cm$^{-1}$ corresponds to the O—H stretching band in free water.

Water can affect the sensing signals of various electronic ammonia sensors. Therefore, the conductance of the protein nanowire sensor was measured over a range of relative humidity, from 45-100%. It was observed that the conductance changed by approximately three orders of magnitude (FIG. 9A). Low-dimension electronic materials are often highly responsive to humidity. Proton conduction assisted by adsorbed water molecules may account for this conductance increase. The protein nanowires adsorb considerable moisture (FIGS. 10A-10B), due to a high-density of hygroscopic functional groups in the constituent amino acids (e.g., carboxyl and amine groups).

Figure 10B:
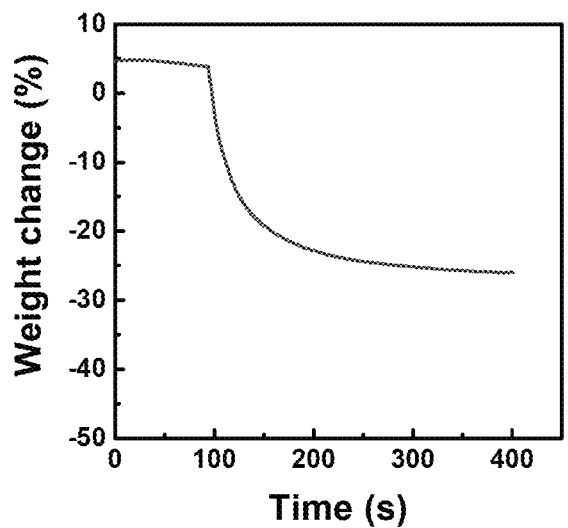
FIG. 10B is a graph of weight percentage of adsorbed moisture in a protein nanowire film measured by quartz crystal microbalance (QCM; 400 C, CH Instruments).

The protein nanowire film was first deposited on the quartz crystal resonator by drop-casting. The mass sensitivity of the QCM originates from the dependence of the oscillation frequency on the total mass of the metal-coated crystal, including any deposited material. The mass change was determined by $$\Delta m = -\Delta f \cdot A \cdot \frac{\sqrt{\mu \rho}}{2 f_0^2},$$

where $f_0$, $A$, $\rho$, $\mu$ are resonant frequency of crystal's fundamental mode, area of the gold disk on the crystal, crystal's density (2.684 g·cm$^{-3}$) and shear modulus of quartz (2.947× 10$^{11}$ g·cm$^{-1}$·s$^{-2}$), respectively. First the mass of the film ($W_{film}$) was determined in a RH~40% environment by QCM. Then, the film was exposed to a RH-0% environment by constant flow of dry air to drive out the adsorbed moisture. During the process, the mass change ($\Delta W_{film}$) that corresponds to the amount of moisture adsorption in the film was continuously monitored (reflected by the resonant-frequency change in QCM). The moisture weight percentage $W_{H_2O}$% in the film was determined by: $W_{H_2O}$% $\Delta W_{film}/W_{film} \times 100$% (FIG. 10B).

Figure 9B:
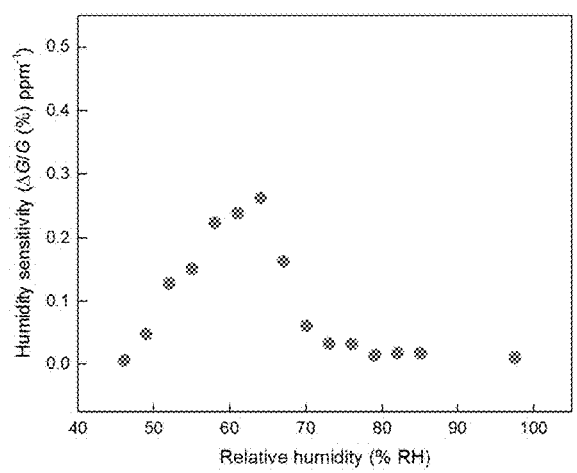
FIG. 9B is a graph of converted humidity sensitivity. Temperature was kept constant at 23° C.

The protein nanowire sensor exhibited a much stronger response to ammonia than to moisture. The maximal sensitivity to water vapor, extrapolated from the current response curve, was ~0.25% ppm$^{-1}$ with an average <0.1% ppm$^{-1}$ (FIG. 9B), whereas the sensitivity to ammonia was 9.4% ppm$^{-1}$ at low concentrations and an average >1% ppm$^{-1}$ over the full range of ammonia concentrations evaluated (FIG. 4B). Additional analysis demonstrated that the sensor response to water vapor was negligible compared to the response to ammonia gas (FIG. 5A).

In order to further evaluate the influence of humidity on ammonia sensing, the ambient humidity inside the vapor chamber was varied (35%-90%) to study the electrical response of the sensor at different initial baseline conductivities after injecting ammonia concentrations of 10 ppm. There was no substantial difference in response to ammonia over this broad range of humidity (FIG. 5B). This converged ammonia sensitivity (e.g., >4% ppm$^{-1}$) indicated that the sensor functions effectively in varied environmental humidity, maintaining excellent sensing performance.

Figure 6:
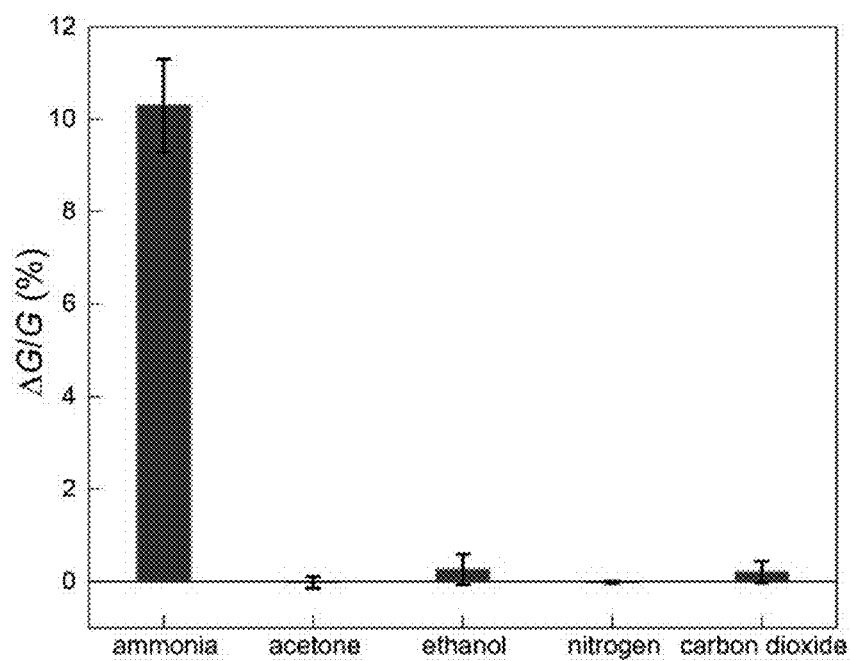
FIG. 6 is a chart of a response of a prototype sensor to 1 ppm of various gases found in human breath using a syringe injection method. Temperature was kept constant at 23° C.

Analysis of ammonia in breath for disease diagnosis requires the ability to discriminate between ammonia and other common breath components. At a concentration of 1 ppm, ammonia gas elicited a percent change in current of 10.3%, significantly higher than the response to acetone, ethanol, carbon dioxide, or nitrogen, with percent changes of 0.13%, 0.33%, 0.23%, and −0.02%, respectively (FIG. 6).

Figure 5A:
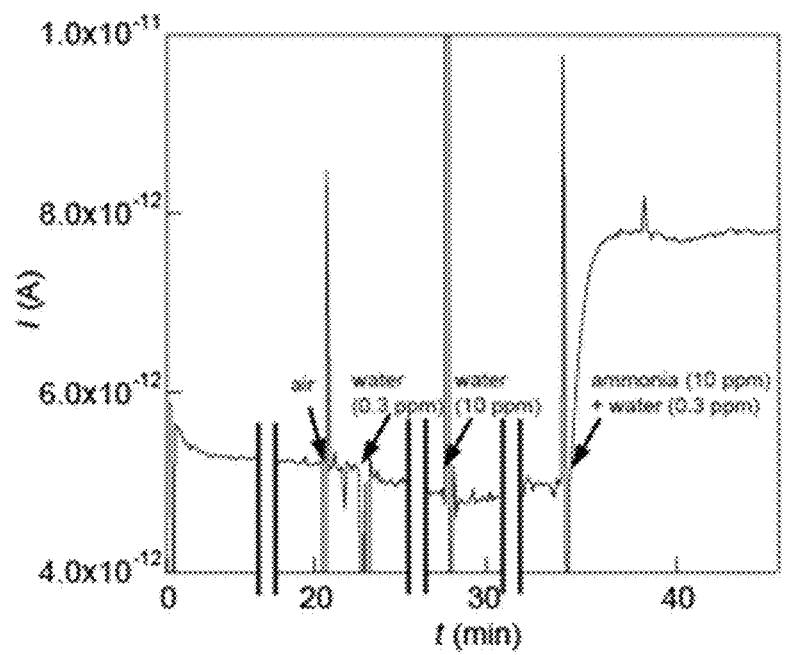
FIG. 5A is a graph of a real-time response of an example protein-nanowire sensor to injected air, pure water vapor (0.3 and 10 ppm), and a mixture containing 10 ppm ammonia+0.3 ppm water vapor. The initial sharp spike for each injection results from an artifact (e.g., mechanical perturbation). Temperature was kept constant at 23° C.
Figure 5B:
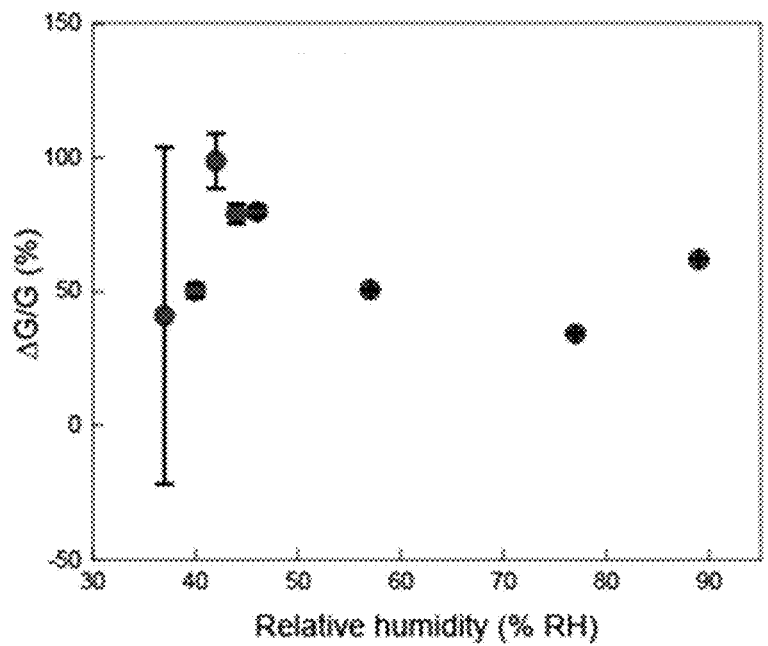
FIG. 5B is a graph illustrating a dose-dependent response of prototype protein nanowire sensors to injected ammonia gas (10 ppm) at various baseline environmental relative humidity levels.

The results demonstrate that protein nanowires can function as highly sensitive, selective, and robust sensors for ammonia with ultra-low power consumption (e.g., ~pW, FIG. 5A). The unique structural and physical/chemical properties of protein nanowires may account for the changes in the protein nanowire thin-film conductivity in the presence of ammonia. Specifically, protein nanowire films contain abundant nanometer or subnanometer pores at the nanowire-nanowire interfaces, providing more opportunities for ammonia gas permeation into the films and more gas-nanowire surface interactions than in existing thin-film sensors. Meanwhile, a high density of hygroscopic groups (e.g., amine and carboxyl groups with an estimated density of 10 nm$^{-1}$) innate to protein nanowires may promote the adsorption of water and ammonia through hydrogen bonding. The small diameter of protein nanowires (e.g., 3 nm) results in a large effective surface area for adsorption. As a result, a substantial adsorption of moisture from the ambient atmosphere was experimentally observed. Surface water adsorption in turn can further enhance ammonia adsorption. Collectively, the protein nanowire film can be highly effective in ammonia adsorption.

Previous studies of *Geobacter* protein nanowires showed that a low pH in the preparation solution can substantially enhance the conductivity in individual nanowires or nanowire thin films. See Adhikari, R. Y., et al. Conductivity of individual *Geobacter* pili. *RSC Advances* 2016. 6, 8354-8357, the entire contents of which are incorporated herein by reference. It was also indicated that a wild-type nanowire film had a p-type conduction trend. See Malvankar, N. S., et al. Tunable metallic-like conductivity in microbial nanowire networks. *Nat. Nanotechnol.* 2011, 6, 573-579, the entire contents of which are incorporated herein by reference.

It is possible that proton-doping mediates the conductance modulation in protein nanowires. Ionization in adsorbed ammonia, which was revealed to be greatly enhanced with a molecular layer of water, can produce protonation sites (e.g., $NH_4^+$) that yield similar doping effects to the protein nanowires. However, the conduction mechanisms in *Geobacter* protein nanowires are not fully understood, which makes it difficult to develop an in-depth mechanistic understanding for how the doping effect from ammonia modifies protein-nanowire film conductivity. In addition, proton transport through the Grotthuass mechanism ($NH_4^+$+ $NH_3 \rightarrow NH_3 + NH_4^+$) may further contribute to the increased conductance. The recent development of a method for producing electrically conductive protein nanowires with *Escherichia coli* can now provide the substantial quantities of protein nanowires required for further mechanistic studies.

Figure 11A:
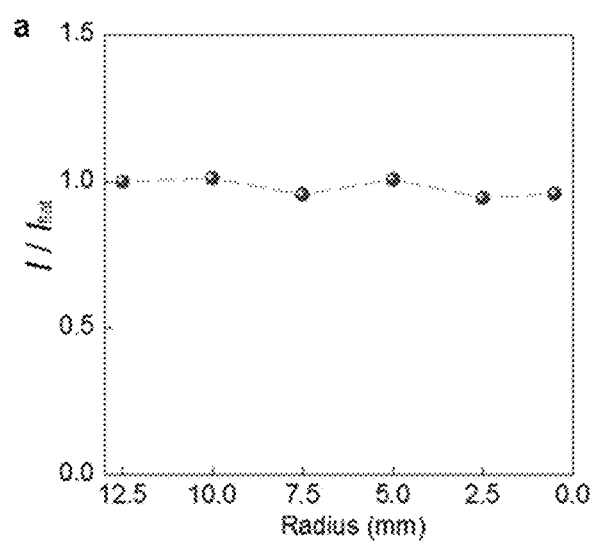
FIG. 11A is a graph of sensor current (I) at different bending radii with respect to current ($I_{flat}$) measured at flat state.
Figure 11B:
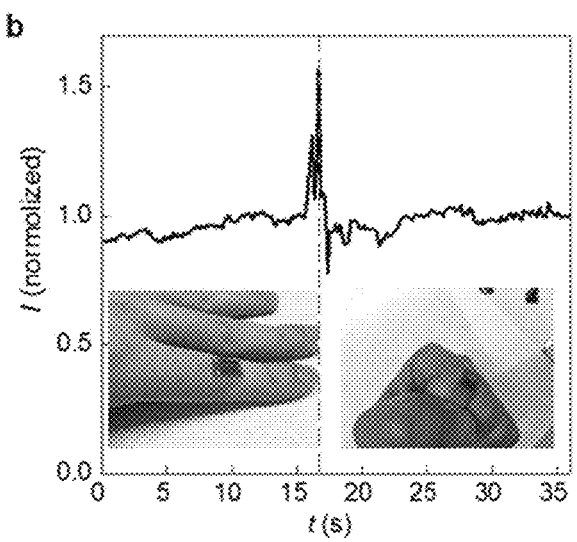
FIG. 11B is a graph of current change in a sensor attached to a bending finger joint. The overall current fluctuation largely came from local RH fluctuation experienced during the bending events. The spike signal came from mechanical perturbation to, e.g., wiring to contacts.

In addition, a protein nanowire sensor integrated on a 25 μm-thick polyimide (PI) substrate can be folded (e.g., at a bending radius <1 mm), demonstrating a negligible change in conductance (FIG. 11A). As a result, the sensor attached to a finger joint experienced minimal mechanical perturbation during bending (FIG. 11A). These preliminary results provide evidence that the protein nanowire sensors can sustain mechanical strain induced from body movements for flexible and wearable applications.

The high sensitivity and selectivity demonstrated here indicate the potential for ammonia sensing in healthcare and environmental applications with use of the devices described. The outer surface of protein nanowires can be further decorated with peptide ligands designed to specifically bind chemicals of interest, providing for broad possibilities to develop sensors for the detection of a wide range of analytes.

Example 4. Fabrication of Protein-Nanowire Sensors for Humidity Detection

Figure 12A:
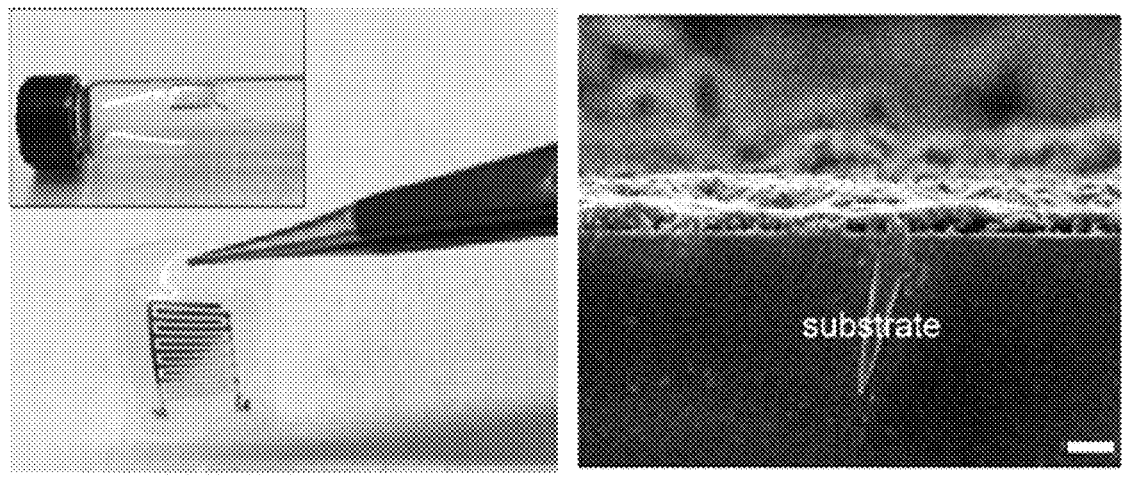
FIG. 12A is a cross-section SEM image (right) of a fabricated flexible protein-nanowire device (left), which conformally covers a glass vial (inset). Scale bar of SEM image, 1 μm.
Figure 12B:
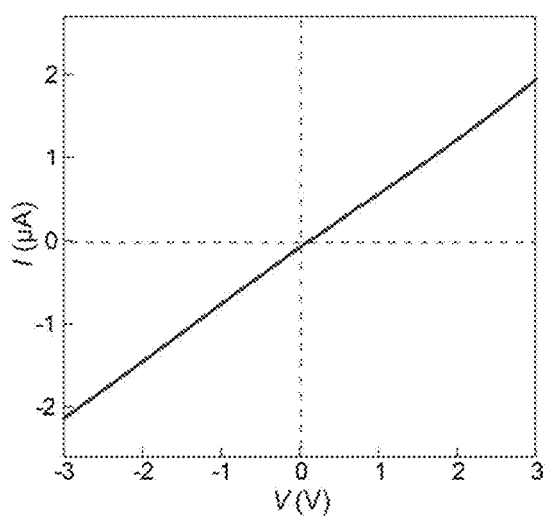
FIG. 12B is a graph of a representative IV curve recorded from a prototype protein-nanowire device under ambient environment (RH-50%).
Figure 12C:
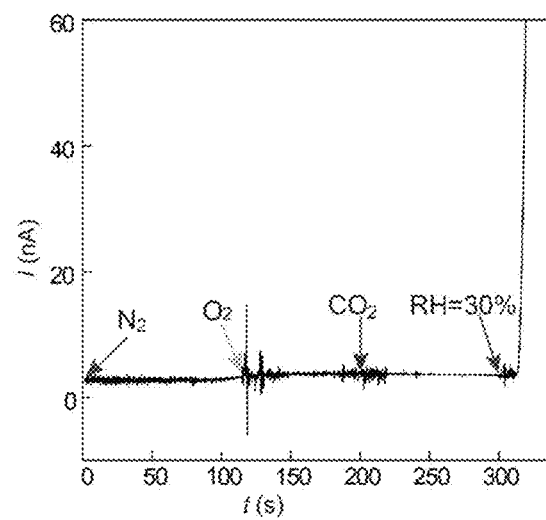
FIG. 12C is a graph of a current response in the protein-nanowire device of FIG. 12B to atmospheric gases. A voltage bias of 1 V was applied to the device.
Figure 16:
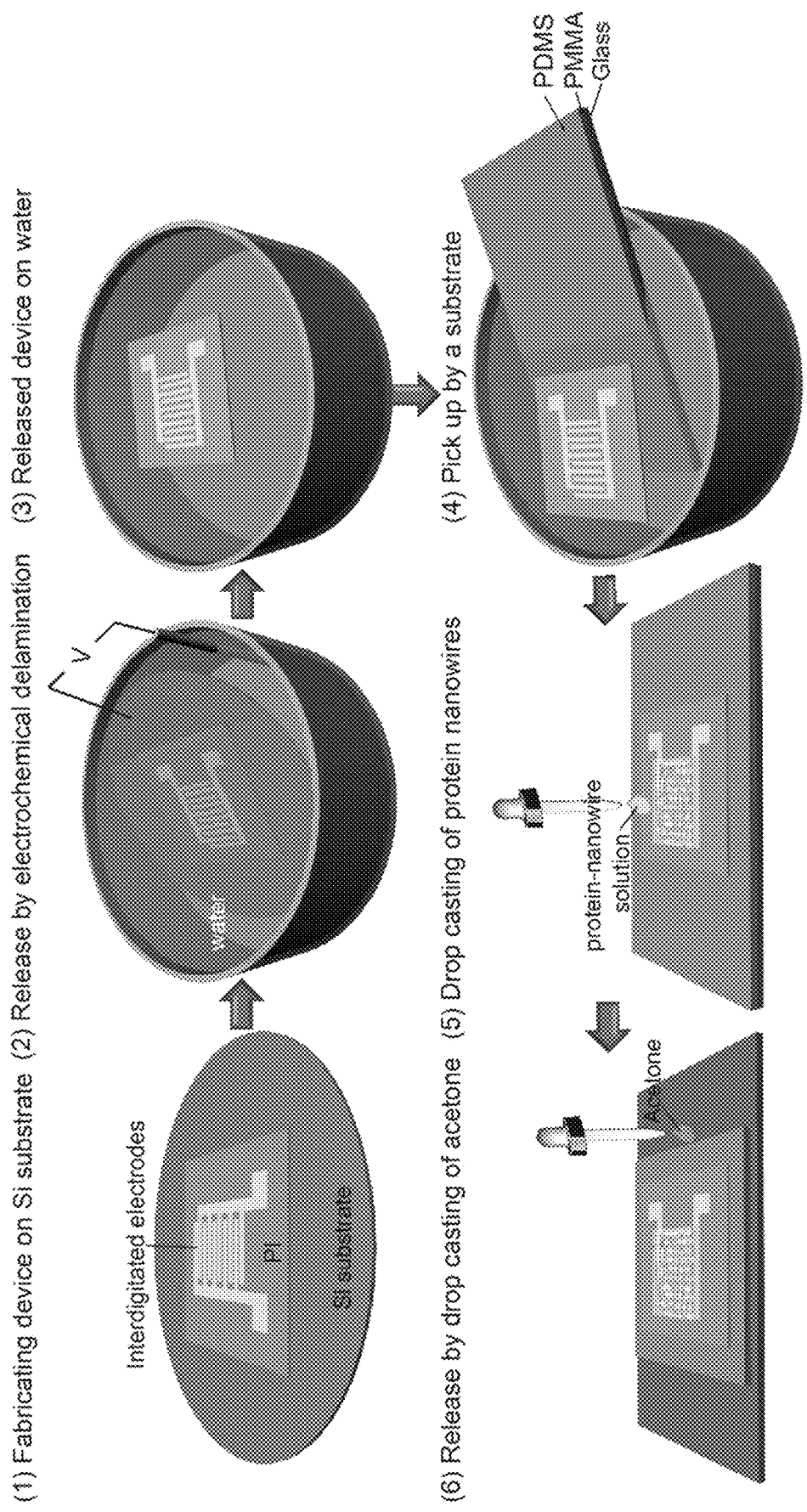
FIG. 16 is a schematic of a device fabrication process.

The prototype sensor device was fabricated by drop casting e-PNs harvested from *G. sulfurreducens* onto a pair of interdigitated Au electrodes patterned on a polyimide (PI) substrate (FIGS. 1, 12A, and 16, Examples 6 and 7). Scanning electron microscopy (SEM) revealed that the nanowire films were ~2 μm thick (FIG. 12A). The current-voltage (IJ-V) response in the ambient environment (FIG. 12B) was nearly linear, consistent with the ohmic-like response previously observed in e-PN films. There was negligible change in current output when the device was exposed to increased concentrations of air components such as $N_2$, $O_2$, and $CO_2$, (FIG. 12C). In contrast, the current increased substantially increased when the relative humidity (RH) was increased (FIG. 12C).

Figure 13A:
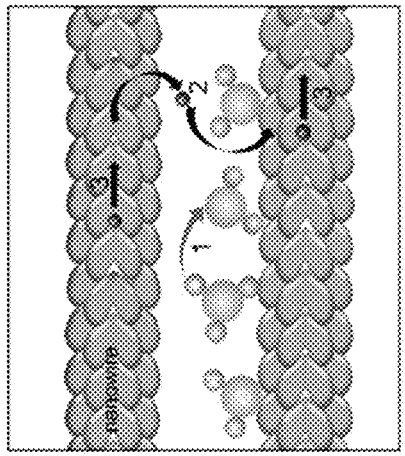
FIG. 13A is a graph of relative current change ($\Delta I/I_o$) in an example nanowire device with respect to the relative humidity (RH). The inset shows the logarithmic scale.
Figure 13B:
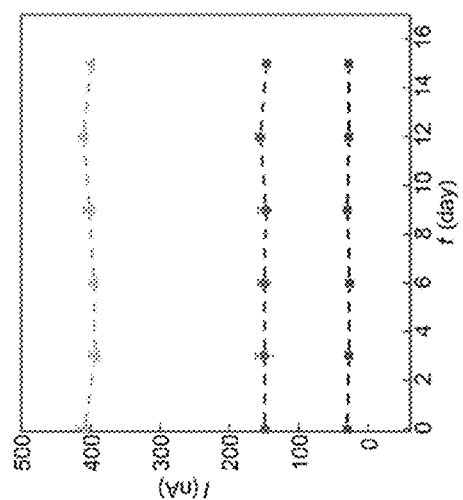
FIG. 13B is a graph of a half-month continuous measurement of the current (I) in an example nanowire device at RH of 40% (bottom line), 60% (middle line) and 80% (top line).

Example 5. Results Obtained from Prototype Protein Nanowire Sensors for Humidity Detection To further quantify the humidity response, the device was exposed to a broad range of RH. Current increased more than two orders of magnitude when the RH was increased from 20% to 95% (FIG. 13A). This current response is comparable to the highest responses of previously described humidity sensors. The current response for different RHs was very stable over 15 days (FIG. 13B).

Figure 17:
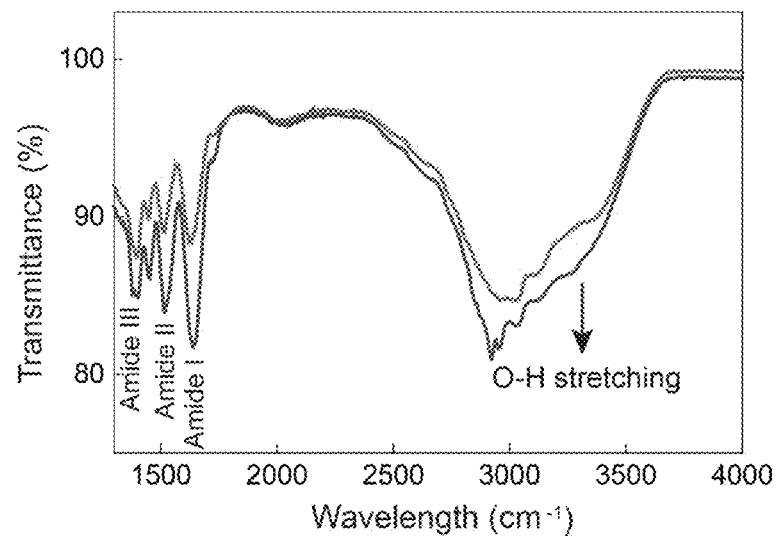
FIG. 17 is a graph of FTIR spectra of example protein nanowire films at relative humidity of 20% (red curve) and 40% (gray curve). The broad peak ~3400 cm$^{-1}$ corresponds to the O—H stretching band in free water, and the increased intensity (gray curve) indicates increased water adsorption in the film at higher relative humidity. The increased intensities in other peaks could be caused by protein segments that became more mobile after moisture filling interstitial voids.
Figure 18A:
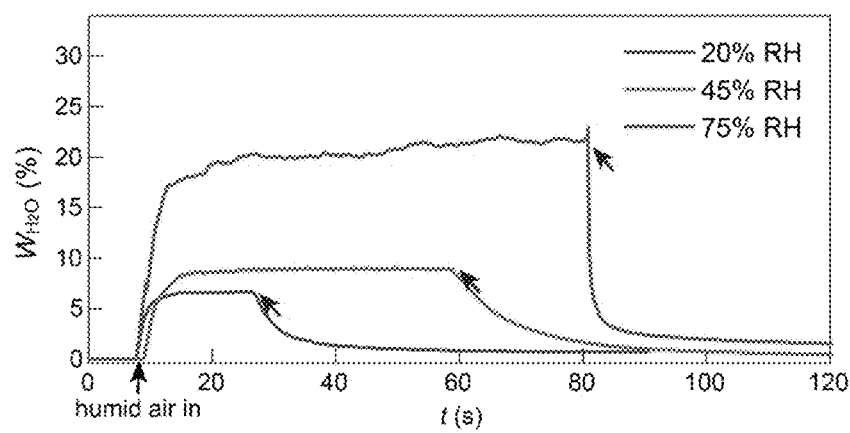
FIG. 18A is a graph of measured moisture content $W_{H_2O}\%$ in a protein-nanowire film (~2 m) at RH of 20%, 45% and 75%. A trend of increased moisture adsorption with increased RH was observed. The black and blue arrows indicating the start of flowing bubbling air and dry air, respectively.
Figure 18B:
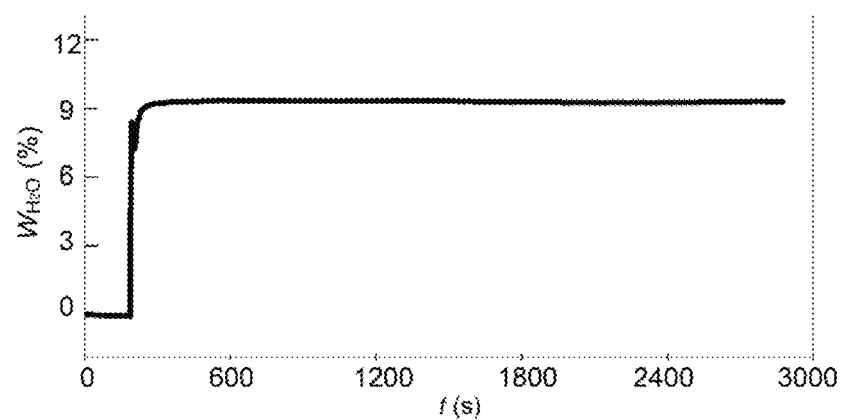
FIG. 18B is a graph of measured moisture content $W_{H_2O}\%$ in a protein-nanowire film at a fixed relative humidity. The adsorbed moisture was measured to be stable in the protein nanowire film at fixed RH (~40%).

Previous studies have demonstrated that e-PN films adsorb moisture from the air. Water adsorption in the e-PN devices described here was confirmed with Fourier-transform infrared spectroscopy (FIG. 17). Quantitative measurements with a quartz crystal microbalance demonstrated that the amount of water adsorbed was dependent on RH, more water was absorbed at higher RH (FIG. 18A). The amount of water adsorbed was stable over time (FIG. 18B). A likely explanation for the water adsorption capacity of the e-PN films is that the abundant carboxyl and hydroxyl groups confer hydrophilicity to this proteinaceous material.

The measurement setup included a gas-purge desiccator cabinet (H42053-0002; Bel-Art) with an inlet and outlet that allow the controlled flow of dry air, a portable hygrometer (Model 8706; REED Instruments) that can real-time monitor the relative humidity (RH) in the cabinet, and a quartz crystal microbalance (QCM; 400 C, CH Instruments) that can monitor the thin-film mass. The protein nanowire film was first deposited on the quartz crystal resonator by drop casting. The mass sensitivity of the QCM originates from the dependence of the oscillation frequency on the total mass of the metal-coated crystal, including any deposited material. The mass change can be determined by $$\Delta m = -\Delta f \cdot A \cdot \frac{\sqrt{\mu \rho}}{2 f_0^2},$$

where $f_0$, $A$, $\rho$, $\mu$ are resonant frequency of crystal's fundamental mode, area of the gold disk on the crystal, crystal's density (2.684 g·cm$^{-3}$) and shear modulus of quartz (2.947× 10$^{11}$ g·cm$^{-1}$·s$^{-2}$), respectively. First, the mass of the dry film ($W_{film}$) was determined in a RH-0% environment by constant dry air flow. Then the flow was switched to bubbling air to increase the RH in the desiccator cabinet. During the process, the mass change ($\Delta W_{film}$) that corresponds to the amount of moisture adsorption in the film, was continuously monitored (reflected by the resonant-frequency change in QCM). The moisture weight percentage $W_{H_2O}$% in the film was determined by: $W_{H_2O}\% = \Delta W_{film}/W_{film} \times 100\%$ (FIGS. 18A-18B).

Figure 13C:
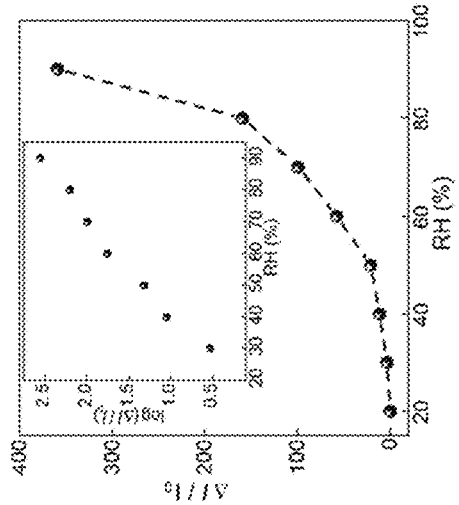
FIG. 13C is a schematic of multiple charge (dots) transfer processes contributing to the overall conduction in a protein-nanowire film. Path '1', '2', and '3' indicate the general external ionic conduction, inter-wire conduction, and intra-wire conduction, respectively.

Adsorbed water molecules can be ionized and can induce ionization in the high-density functional groups in the protein nanowires. This ionization can enhance the conductivity of e-PN films in several ways (FIG. 13C). Most simply, the ionized mobile species will generally contribute to the extrinsic ionic conduction. For example, adsorbed water molecules can form a relay network for proton transport through the Grotthuss mechanism for enhanced conduction. Also, the ionized species can substantially enhance electron transfer between wires within the film. The conductivity of individual e-PNs is >10$^3$ fold higher than e-PN films due to wire-to-wire resistance. Furthermore, water adsorption can modify the surface charge state of diverse materials. The large surface area and high-density of functional groups in e-PNs may enhance this effect. The large impact of 'proton doping' on e-PNs conductivity suggests that surface charge state is an important factor in determining the conduction in individual e-PNs, although the molecular mechanisms warrant further investigation.

Figure 13D:
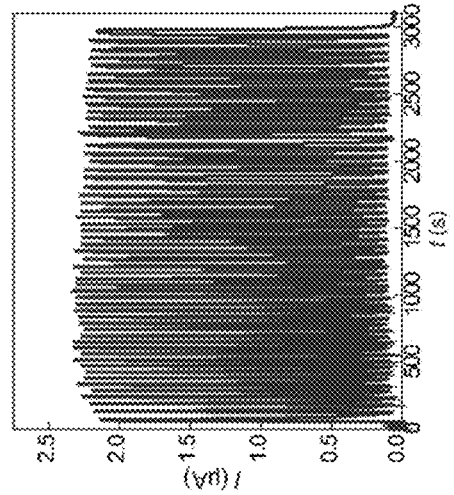
FIG. 13D is a graph of temporal correlation between moisture adsorption ($\Delta W_{H2O}$, black curve) in a protein-nanowire film and current change ($\Delta I$, grey curve) in an example nanowire device when RH changed from 30% to 90% by a bubbling method. The values are normalized.
Figure 13E:
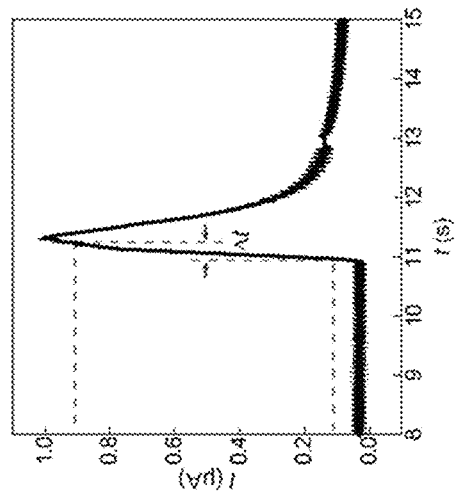
FIG. 13E is a graph of a response time ($\Delta t$) of an example nanowire device, defined as the rising time from 10% to 90% of the signal peak, to a breath.
Figure 13F:
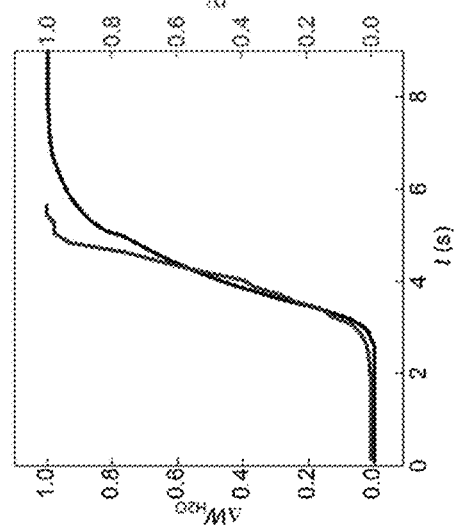
FIG. 13F is a graph of a current response to 55 continuous breaths in the example device. All the data was obtained at a bias of 1 V.

There was a close correspondence between the time required for water adsorption in the e-PN films and the current response (FIG. 13D), providing further support that water adsorption induced a change in conductance of the e-PN films (FIG. 13C). There was a very fast response (~150±17 ms (n=5)) to breathing on the device, which increases the RH at the e-PN film surface (FIG. 13E). This response is among the fastest of known humidity sensors. The rapid change of the water adsorption in response to an environmental humidity change indicates that the water in the e-PN film maintains a dynamic equilibrium with the environment. This finding is consistent with the previously documented rapid adsorption-desorption exchange of water molecules at air-solid interfaces. When the local RH declined following the end of the breath the conductance was rapidly restored to the initial baseline. Breath sensing was repeatable and reproducible (FIG. 13D).

Prototype wearable nanowire sensors were fabricated on a PI layer, further supported by a polydimethylsiloxane (PDMS) substrate that can conform to the body surface (FIG. 16). Prototype devices fabricated on a flexible PDMS patch were able to conformally cover surface curvature (diameter ~5 mm) of a glass rad and human skin. Devices placed close to the nose responded to the local RH change created by the breath, providing a real-time monitoring of the respiratory rate (FIG. 14A) that increased during exercise compared to a resting state.

Skin hydration levels can be indicative of various health and disease states. Skin hydration leads to RH change close to the skin surface, thus a moisture sensor can also monitor the hydration state. The e-PN-based sensor could detect local RH differences at (i) different body locations (FIG. 14B) and (ii) different body states (FIG. 14C). These results demonstrate that the sensor arrays can provide both spatial and temporal mapping of body hydration state for comprehensive diagnostics.

Orthogonal to the surface distribution of RH, is a vertical RH gradient with RH decreasing as distance from the skin increases. The high sensitivity for RH enabled a dynamic detection of a finger movement above the sensor, in which the translational and vertical distance of the fingertip was inferred through the sensing signal (FIG. 14D). Quantitative analysis revealed that the nanowire sensor responded to a RH gradient from the finger, with an approximately linear decrease in the sensing signal with the increase in distance from the fingertip (FIG. 14E). A finger distance as far as 10 mm was readily detected. Previously, tactile sensors have been integrated in arrays to map pressure distribution and for intelligent object differentiation. By employing a similar concept, the protein-nanowire sensors may be used to realize noncontact perception for performance augmentation in intelligent applications (FIG. 14F, upper left). In a proof-of-concept demonstration with a 4×4 sensor matrix (FIG. 14F, bottom left), the relative signal in each sensor reflected its relative position to the fingertip placed above the matrix and this data enabled a reconstruction and location of the fingertip (FIG. 14F).

Moisture gradients that form in e-PN films with an asymmetric vertical device structure in the ambient environment yield electric current outputs. Therefore, it was of interest to determine whether an external humidity/moisture gradient in symmetric device structure might induce current in an unbiased device. Various energy conversion, harvesting, transmission and storage strategies have been developed to support the continuous powering of wearable devices, because harvesting energy from the environment yields clean and sustainable powering. Humidity carries both electrostatic and kinetic energy that can be converted into electric energy. Specifically, a moisture gradient in conductive porous materials can either induce an ionization gradient for charge diffusion or nanofluidic water transport that carries charge flow, both of which generate electric current.

Figure 15A:
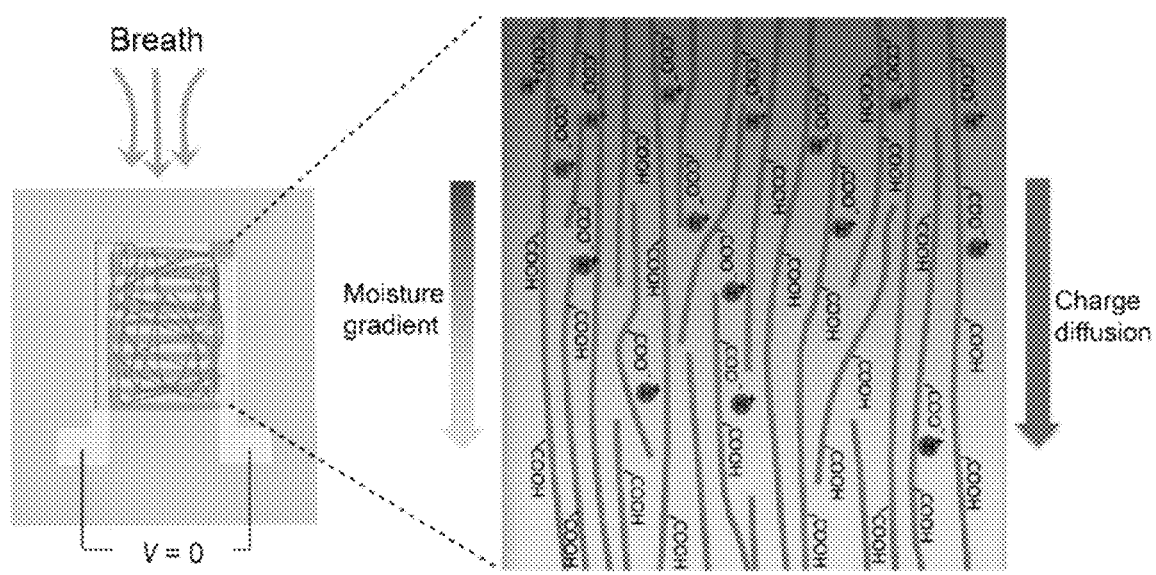
FIG. 15A is a schematic of an unbiased protein-nanowire device exposed to a humidity gradient (e.g., upon a breath). The humidity gradient induces a moisture-adsorption gradient in the film, which further generates an ionization gradient. The ionization gradient leads to a gradient in the mobile charge species (e.g., protons against an immobile background COOH⁻), which diffuse to generate current.
Figure 15B:
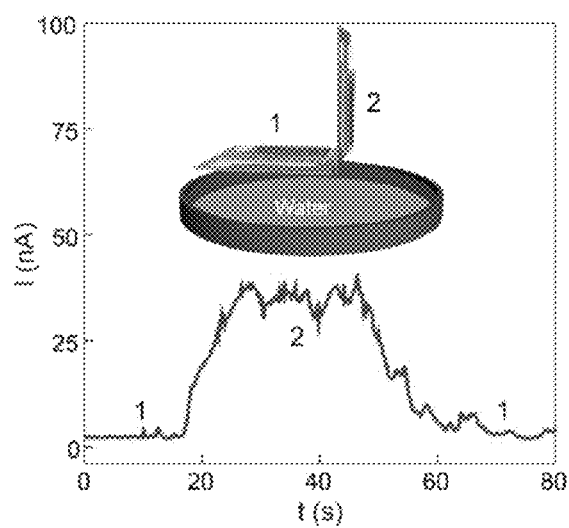
FIG. 15B is a graph of current produced by an example nanowire device in horizontal and vertical positions. The nanowire device produced more current when it was rotated to a vertical position above a wafer surface (inset).
Figure 15C:
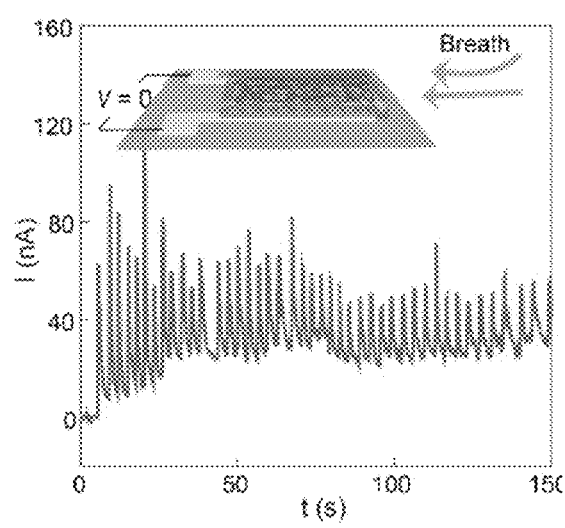
FIG. 15C is a graph of current produced by an example an unbiased protein-nanowire device, which served as a self-powered respiratory sensor by converting the humidity gradient of a breath into a current spike.

The e-PN films have high-density nanoscale pores or channels for moisture adsorption and transport (FIGS. 18A, 19B). The high-density surface functional groups (e.g., carboxyl and hydroxyl) in the nanowires will produce mobile charges (e.g. protons) upon moisture-induced ionization. If a moisture gradient is induced in the film, the resultant ionization gradient induces charge diffusion in the mobile species and hence a nonlocal electric current flow (FIG. 15A). For example, increasing the humidity gradient by rotating the device from a parallel to a perpendicular position to the water surface increased the current signal in an unbiased sensor (FIG. 15B). An unbiased nanowire sensor placed close to the nose, where a humidity gradient was anticipated from exhaling, produced a peak current signal ~100 nA with the periodicity matching to the breathing rate (FIG. 15C), resulting in self-powered respiratory monitoring. The self-powered humidity sensor can be readily converted to a wearable energy generator to charge up a capacitor for powering electronics (FIG. 20).

The high-performance humidity sensing demonstrated here has potential applications in physiological monitoring and remote body tracking with the added possibility of powerless sensing. The sensing capabilities of e-PN based devices can be used for the detection and quantification of a broad range of medically and environmentally significant chemicals/metabolites because the outer surface of e-PNs can be functionalized peptide ligands designed to specifically bind analytes of interest.

Example 6. Materials and Methods: Synthesis and Purification of Protein Nanowires

*Geobacter sulfurreducens* was routinely cultured at 25° C. under strict anaerobic conditions (80/20 $N_2$—$CO_2$) in chemostatsin[1] the previously described[2] mineral based medium containing acetate (15 mM) as the electron donor and fumarate (40 mM) as the electron acceptor. Cells were collected with centrifugation and re-suspended in 150 mM ethanolamine buffer (pH 10.5). The protein nanowires were harvested and purified as previously described. Briefly, protein nanowires were sheared from the cells in a blender. Cells were removed with centrifugation. The protein nanowires in the supernatant were precipitated with ammonium sulfate followed by centrifugation. The precipitate was re-suspended in ethanolamine buffer and additional debris was removed with centrifugation. The protein nanowires were collected with a second 10% ammonium sulfate precipitation and subsequent centrifugation at 13,000 g. The protein nanowires were re-suspended in ethanolamine buffer. This protein-nanowire preparation was dialyzed against deionized water to remove the buffer and stored at 4° C. The resultant nanowire preparation yielded a measured pH-9.

Example 7. Materials and Methods: Device Fabrication

The fabrication process of a protein-nanowire sensor was as follows (FIG. 16). (1) A thin layer of polyimide (PI-2545; HD Microsystems) was spin coated (3000 rpm) on a Si wafer (3 inch P(100) 0-100 Ω·cm; UniversityWafer Inc.), followed by soft baking at 150° C. for 5 min and curing at 250° C. in an oven for 2 hr. Interdigitated electrodes were defined on PI film through standard photolithography, metal evaporation (Au/Cr=30/5 nm) and lift-off processes. The 20 interdigitated electrodes in each device typically had a width~300 μm, length~0.5 cm, and intra-electrode separation ~100 μm. (2) The PI film with interdigitated electrodes was released from the Si substrate by using an electrochemical etching-assisted delamination method. (3) The released PI layer, with defined electrodes, was floating on a water surface. (4) A pick-up substrate was then prepared as follows. First, a thin layer of polymethyl methacrylate (PMMA, 950 C2; MicroChem) was spin coated (1000 rpm, 60 s) on a glass slide and baked (100° C., 2 min). Then a layer of polydimethylsiloxane (PDMS, Sylgard 184, 10:1 mix ratio; Dow Corning) was spin coated (1000 rpm, 60 s) on the PMMA layer, yielding an estimated ~80 μm thickness. The PDMS layer was curled at 90° C. for 1 hr. The PI film floating on the water was picked up by the glass slide coated with PDMS/PMMA layers. (5) Protein nanowire solution (~100 μl) was drop casted on the interdigitated electrode area, which was then placed on a hotplate (~80° C.) to facilitate solvent (water) evaporation to form protein-nanowire film. (6) A patch area containing the nanowire device was carved out, and the patch was then released from the glass substrate by using acetone droplet to dissolve the PMMA layer. The electrodes in the device were wired using silver paste for electrical characterizations (the wiring by silver paste was not shown in prototyped device figures in the main text).

Example 8. Materials and Methods: Humidity Control

The relative humidity (RH) was controlled through two approaches. First, carrier gases (e.g., $N_2$, $O_2$, air) bubbling through a water-containing conical flask was led into a gas-purge desiccator cabinet (H42053-0002; Bel-91 Art), and the flow rate was adjusted to control the RH in the desiccator cabinet. The RH was real-time monitored by a hygrometer (Model 8706; REED Instruments). The bubbler method was used for controlled RH in measurements of moisture adsorption and device response time. Alternatively, RH was controlled by tuning the equilibrium vapor pressure of sulfuric acid solutions, i.e., the concentration of sulfuric acid (for FTIR measurements).

Example 9. Materials and Methods: Device and Material Characterizations

The thicknesses in protein nanowire films were measured by a desktop scanning electron microscope (SEM, EM-30 Plus; Element Pi). The high-resolution nanowire networks were imaged by using a transmission electron microscope (TEM, JEM-2200FS; JEOL). The $H_2O$ bonding spectra in protein nanowires were performed by a Fourier-transform infrared spectroscopy (FTIR; Perkin Elmer) equipped with a universal attenuated-total-reflection (ATR) sampling accessory. I-V and I-t curves were measured by using a source meter (Keithley 2401; Tektronix) interfaced with computerized recording software.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A gas sensor comprising: a biomaterial comprising electrically-conductive protein nanowires, wherein the protein nanowires comprise a structure assembled from protein monomers having an amino acid sequence selected from SEQ ID NO:1-SEQ ID NO:33 and variants thereof; and at least two electrodes in operative arrangement with the protein nanowires and configured to provide a signal indicative of a change in conductivity of the protein nanowires, the conductivity of the protein nanowires being responsive to a change in concentration of a gas exposed to the biomaterial.

2. The gas sensor of claim 1, wherein conductivity of the protein nanowires varies in response to changes in ammonia concentration.

3. The gas sensor of claim 2, wherein the changes in ammonia concentration are within a range of about 5 ppb to about 15,000 ppb.

4. The gas sensor of claim 1, wherein conductivity of the protein nanowires varies in response to changes in humidity.

5. The gas sensor of claim 4, wherein the changes in humidity are relative changes in humidity of between about 5% to about 100%.

6. The gas sensor of claim 1, wherein the protein nanowires are configured to yield an electrical output in response to exposure to moisture and without an applied voltage to the biomaterial.

7. The gas sensor of claim 1, further comprising an energy store.

8. The gas sensor of claim 1, wherein the at least two electrodes are configured to apply a voltage to the biomaterial.

9. The gas sensor of claim 8, wherein an applied voltage is of about 0.1 V to about 5 V.

10. The gas sensor of claim 1, wherein the protein nanowires comprise a pilus structure, a cytochrome filament structure, or a combination thereof.

11. The gas sensor of claim 10, wherein the pilus structure is a type IV pilus structure.

12. The gas sensor of claim 1, wherein the protein nanowires are of the bacterium *G. sulfurreducens*.

13. The gas sensor of claim 1, further comprising a flexible substrate on which the film and the at least two electrodes are disposed.

14. The gas sensor of claim 1, wherein the at least two electrodes are interdigitated.

15. The gas sensor of claim 1, wherein the biomaterial comprises a composite of protein nanowires and at least one other material.

16. The gas sensor of claim 15, wherein the at least one other material is an organic or inorganic material that modifies a conductive property of the protein nanowires, confers structural support to the protein nanowires, or a combination thereof.

17. The gas sensor of claim 1, wherein the biomaterial is a flexible film.

18. The gas sensor of claim 17, wherein the film has a thickness of about 2 nm to about 500 nm.

19. A wearable sensor comprising: a gas sensor comprising: a biomaterial comprising electrically-conductive protein nanowires, wherein the protein nanowires comprise a structure assembled from protein monomers having an amino acid sequence selected from SEQ ID NO:1-SEQ ID NO:33 and variants thereof, and at least two electrodes in operative arrangement with the protein nanowires and configured to provide a signal indicative of a change in conductivity of the protein nanowires, the conductivity of the protein nanowires being responsive to a change in concentration of a gas exposed to the biomaterial; and an attachment mechanism.

\* \* \* \* \*